(12) United States Patent
Bogert et al.

(10) Patent No.: US 8,066,758 B2
(45) Date of Patent: Nov. 29, 2011

(54) VASCULAR GRAFT WITH KINK RESISTANCE AFTER CLAMPING

(75) Inventors: David L. Bogert, Tempe, AZ (US); Jamie Abbott, Mesa, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 861 days.

(21) Appl. No.: 11/917,135

(22) PCT Filed: Dec. 28, 2005

(86) PCT No.: PCT/US2005/046763
§ 371 (c)(1),
(2), (4) Date: Jan. 17, 2008

(87) PCT Pub. No.: WO2007/001472
PCT Pub. Date: Jan. 4, 2007

(65) Prior Publication Data
US 2010/0179642 A1    Jul. 15, 2010

Related U.S. Application Data

(63) Continuation-in-part of application No. PCT/US2005/031186, filed on Aug. 30, 2005.

(60) Provisional application No. 60/692,172, filed on Jun. 17, 2005.

(51) Int. Cl.
*A61F 2/06* (2006.01)

(52) U.S. Cl. ................ 623/1.13; 623/1.32; 606/194

(58) Field of Classification Search .......... 623/1.13, 623/1.3, 1.31; 606/191, 194, 198; *A61F 2/06*
See application file for complete search history.

(56) References Cited

U.S. PATENT DOCUMENTS

| | | |
|---|---|---|
| 3,105,492 A | 10/1963 | Jeckel |
| 4,130,904 A | 12/1978 | Whalen |
| RE31,618 E | 7/1984 | Mano et al. |
| 4,550,447 A | 11/1985 | Seiler, Jr. et al. |
| 4,604,762 A | 8/1986 | Robinson |
| 4,619,641 A | 10/1986 | Schanzer |
| 4,718,907 A | 1/1988 | Karwoski et al. |
| 4,731,073 A | 3/1988 | Robinson |

(Continued)

FOREIGN PATENT DOCUMENTS

JP    2003-511196 A    3/2003

(Continued)

OTHER PUBLICATIONS

James et al., "In Vivo Patency of Endothelial Cell-Lined ePTFE Prostheses in an Ovine Model"; Artif Organs, Aug. 1992; 16(4):346-53.

(Continued)

*Primary Examiner* — Thomas J Sweet
*Assistant Examiner* — Jason-Dennis Stewart
(74) *Attorney, Agent, or Firm* — Rutan & Tucker, LLP

(57) ABSTRACT

A self-sealing vascular graft with kink resistance is described. The vascular graft includes a substrate that can be a PTFE, having a self-sealing region that may include several layers of material. The central section of the vascular graft may be constructed differently from surrounding self-sealing regions, in order to provide kink resistance following the clamping of the graft. Also described is a graft with a flared cuff attached to one or both ends, the attachment or transition region including reinforcement beading.

18 Claims, 16 Drawing Sheets

U.S. PATENT DOCUMENTS

| | | |
|---|---|---|
| 4,733,665 A | 3/1988 | Palmaz |
| 4,739,013 A | 4/1988 | Pinchuk |
| 4,743,252 A | 5/1988 | Martin, Jr. et al. |
| 4,810,749 A | 3/1989 | Pinchuk |
| 4,816,339 A | 3/1989 | Tu et al. |
| 4,857,069 A | 8/1989 | Kira et al. |
| 4,955,899 A | 9/1990 | Della Corna et al. |
| 5,024,671 A | 6/1991 | Tu et al. |
| 5,061,276 A | 10/1991 | Tu et al. |
| 5,116,360 A | 5/1992 | Pinchuk et al. |
| 5,133,742 A | 7/1992 | Pinchuk |
| 5,152,782 A | 10/1992 | Kowligi et al. |
| 5,192,310 A | 3/1993 | Herweck et al. |
| 5,229,431 A | 7/1993 | Pinchuk |
| 5,354,329 A | 10/1994 | Whalen |
| 5,453,235 A | 9/1995 | Calcote et al. |
| 5,507,769 A | 4/1996 | Marin et al. |
| 5,527,353 A | 6/1996 | Schmitt |
| 5,556,426 A | 9/1996 | Popadiuk et al. |
| 5,607,478 A | 3/1997 | Lentz et al. |
| 5,609,624 A | 3/1997 | Kalis |
| 5,620,763 A | 4/1997 | House et al. |
| 5,628,782 A | 5/1997 | Myers et al. |
| 5,641,373 A | 6/1997 | Shannon et al. |
| 5,641,443 A | 6/1997 | Calcote et al. |
| 5,665,114 A | 9/1997 | Weadock et al. |
| 5,700,287 A | 12/1997 | Myers et al. |
| 5,707,386 A | 1/1998 | Schnepp-Pesch et al. |
| 5,716,393 A | 2/1998 | Lindenberg et al. |
| 5,716,395 A | 2/1998 | Myers et al. |
| 5,716,660 A | 2/1998 | Weadock et al. |
| 5,800,510 A | 9/1998 | Schmitt |
| 5,800,512 A | 9/1998 | Lentz et al. |
| 5,824,050 A | 10/1998 | Karwoski et al. |
| 5,827,327 A | 10/1998 | McHaney et al. |
| 5,840,240 A | 11/1998 | Stenoien et al. |
| 5,843,173 A | 12/1998 | Shannon et al. |
| 5,851,229 A | 12/1998 | Lentz et al. |
| 5,851,230 A | 12/1998 | Weadock et al. |
| 5,860,999 A | 1/1999 | Schnepp-Pesch et al. |
| 5,861,026 A | 1/1999 | Harris et al. |
| 5,866,217 A | 2/1999 | Stenoien et al. |
| 5,897,587 A | 4/1999 | Martakos et al. |
| 5,904,967 A | 5/1999 | Ezaki et al. |
| 5,910,168 A | 6/1999 | Myers et al. |
| 5,931,865 A | 8/1999 | Silverman et al. |
| 5,976,192 A | 11/1999 | McIntyre et al. |
| 6,001,125 A | 12/1999 | Golds et al. |
| 6,010,529 A | 1/2000 | Herweck et al. |
| 6,019,788 A | 2/2000 | Butters et al. |
| 6,022,335 A * | 2/2000 | Ramadan .................... 604/93.01 |
| 6,036,724 A | 3/2000 | Lentz et al. |
| 6,039,755 A | 3/2000 | Edwin et al. |
| 6,042,666 A | 3/2000 | Karwoski et al. |
| 6,053,941 A | 4/2000 | Lindenberg et al. |
| 6,053,943 A * | 4/2000 | Edwin et al. .................. 623/1.25 |
| 6,056,970 A | 5/2000 | Greenawalt et al. |
| 6,080,198 A | 6/2000 | Lentz et al. |
| 6,099,557 A | 8/2000 | Schmitt |
| 6,102,884 A | 8/2000 | Squitieri |
| 6,124,523 A | 9/2000 | Banas et al. |
| 6,162,244 A | 12/2000 | Braun et al. |
| 6,187,038 B1 | 2/2001 | Sullivan et al. |
| 6,187,039 B1 | 2/2001 | Hiles et al. |
| 6,190,590 B1 | 2/2001 | Randall et al. |
| 6,203,735 B1 | 3/2001 | Edwin et al. |
| 6,221,101 B1 | 4/2001 | Harris et al. |
| 6,261,257 B1 | 7/2001 | Uflacker et al. |
| 6,267,834 B1 | 7/2001 | Shannon et al. |
| 6,270,523 B1 | 8/2001 | Herweck et al. |
| 6,273,912 B1 | 8/2001 | Scholz et al. |
| 6,287,337 B1 | 9/2001 | Martakos et al. |
| 6,315,791 B1 | 11/2001 | Gingras et al. |
| 6,319,279 B1 | 11/2001 | Shannon et al. |
| 6,328,762 B1 | 12/2001 | Anderson et al. |
| 6,355,063 B1 | 3/2002 | Calcote |
| 6,368,347 B1 | 4/2002 | Maini et al. |
| 6,383,214 B1 | 5/2002 | Banas et al. |
| 6,416,537 B1 | 7/2002 | Martakos et al. |
| 6,428,571 B1 | 8/2002 | Lentz et al. |
| 6,436,135 B1 | 8/2002 | Goldfarb |
| 6,451,047 B2 | 9/2002 | McCrea et al. |
| 6,514,196 B1 | 2/2003 | Sullivan et al. |
| 6,534,084 B1 | 3/2003 | Vyakarnam et al. |
| 6,547,820 B1 | 4/2003 | Staudenmeier |
| 6,572,647 B1 | 6/2003 | Supper et al. |
| 6,589,278 B1 | 7/2003 | Harris et al. |
| 6,589,468 B1 | 7/2003 | Schmitt |
| 6,596,023 B1 | 7/2003 | Nunez et al. |
| 6,712,919 B2 | 3/2004 | Ruefer et al. |
| 6,716,239 B2 | 4/2004 | Sowinski et al. |
| 6,719,783 B2 | 4/2004 | Lentz et al. |
| 6,746,480 B2 | 6/2004 | Scholz et al. |
| 6,756,007 B2 | 6/2004 | Pletzer et al. |
| 6,786,920 B2 | 9/2004 | Shannon et al. |
| 6,790,226 B2 | 9/2004 | Edwin et al. |
| 6,797,217 B2 | 9/2004 | McCrea et al. |
| 6,814,753 B2 | 11/2004 | Schmitt |
| 6,821,295 B1 * | 11/2004 | Farrar .......................... 623/1.31 |
| 6,827,737 B2 | 12/2004 | Hill et al. |
| 6,863,686 B2 | 3/2005 | Shannon et al. |
| 6,926,735 B2 | 8/2005 | Henderson |
| 7,244,271 B2 | 7/2007 | Lentz et al. |
| 2001/0018609 A1 | 8/2001 | Smith |
| 2002/0065552 A1 | 5/2002 | Jayaraman et al. |
| 2002/0091439 A1 * | 7/2002 | Baker et al. .................. 623/1.36 |
| 2002/0138136 A1 | 9/2002 | Chandresekaran et al. |
| 2002/0193869 A1 | 12/2002 | Dang |
| 2003/0004559 A1 | 1/2003 | Lentz et al. |
| 2003/0004563 A1 | 1/2003 | Jackson et al. |
| 2003/0017775 A1 | 1/2003 | Sowinski et al. |
| 2003/0027775 A1 | 2/2003 | Wallace |
| 2003/0100859 A1 | 5/2003 | Henderson et al. |
| 2003/0139806 A1 | 7/2003 | Haverkost et al. |
| 2003/0204242 A1 | 10/2003 | Zarins et al. |
| 2004/0015228 A1 | 1/2004 | Lombardi et al. |
| 2004/0024442 A1 | 2/2004 | Sowinski et al. |
| 2004/0033364 A1 | 2/2004 | Spiridigliozzi et al. |
| 2004/0049264 A1 | 3/2004 | Sowinski et al. |
| 2004/0054406 A1 | 3/2004 | Dubson et al. |
| 2004/0064181 A1 | 4/2004 | Harris et al. |
| 2004/0082989 A1 | 4/2004 | Cook et al. |
| 2004/0122507 A1 | 6/2004 | Henderson |
| 2004/0122509 A1 | 6/2004 | Brodeur |
| 2004/0182511 A1 | 9/2004 | Rakos et al. |
| 2004/0193242 A1 | 9/2004 | Lentz et al. |
| 2004/0210302 A1 | 10/2004 | Scholz et al. |
| 2004/0215337 A1 | 10/2004 | Hain et al. |
| 2004/0244442 A1 | 12/2004 | Shiao et al. |
| 2005/0064224 A1 * | 3/2005 | Bavaro et al. ................. 428/615 |
| 2005/0246012 A1 | 11/2005 | Henderson |
| 2006/0116755 A1 | 6/2006 | Stinson |
| 2006/0259133 A1 | 11/2006 | Sowinski et al. |
| 2007/0123968 A1 | 5/2007 | Weinberg |
| 2007/0204445 A1 | 9/2007 | Hood et al. |
| 2007/0244539 A1 | 10/2007 | Lentz et al. |
| 2008/0027534 A1 | 1/2008 | Edwin et al. |
| 2009/0171436 A1 | 7/2009 | Casanova et al. |

FOREIGN PATENT DOCUMENTS

| | | |
|---|---|---|
| WO | 9721401 A1 | 6/1997 |
| WO | 0128456 A1 | 4/2001 |
| WO | 2004096307 A1 | 11/2004 |

OTHER PUBLICATIONS

Kohler et al., "Dialysis Access Failure: A Sheep Model of Rapid Stenosis", J Vasc Surg., Oct. 1999; 30(4):744-51.

Tillman et al, "Platelet Function and Coagulation Parameters in Sheep During Experimental Vascular Surgery", Lab Anim Sci., Jun. 1981; 31(3):263-7.

PCT Search Report, Application No. PCT/US05/46763, Apr. 30, 2007.

JP 2007-530364 filed Aug. 30, 2005 Office Action dated Oct. 19, 2010.

PCT/US2005/031186 filed Aug. 30, 2005 International Preliminary Report on Patentability dated Feb. 28, 2007.

PCT/US2005/031186 filed Aug. 30, 2005 Search Report dated Feb. 6, 2007.
PCT/US2005/031186 filed Aug. 30, 2005 Written Opinion dated Feb. 6, 2007.
PCT/US2005/046763 filed Dec. 28, 2005 International Preliminary Report on Patentability dated Dec. 17, 2007.
PCT/US2005/046763 filed Dec. 28, 2005 Written Opinion dated Apr. 30, 2007.
U.S. Appl. No. 11/661,250, filed Mar. 27, 2007 Final Office Action dated Oct. 14, 2009.
U.S. Appl. No. 11/661,250, filed Mar. 27, 2007 Non-Final Office Action dated Apr. 1, 2009.
U.S. Appl. No. 11/661,250, filed Mar. 27, 2007 Non-Final Office Action dated Sep. 18, 2008.
EP 06839788.4 filed on Aug. 5, 2008 EP Search Report dated Dec. 28, 2009.
EP 06839788.4 filed on Aug. 5, 2008 Office Action dated Jul. 13, 2010.
PCT/US2006/060704 filed on Nov. 9, 2006 International Preliminary Report on Patentability dated May 14, 2006.
PCT/US2006/060704 filed on Nov. 9, 2006 Search Report dated Nov. 1, 2007.
PCT/US2006/060704 filed on Nov. 9, 2006 Written Opinion dated Nov. 1, 2007.
JP 2008-516811 filed Dec. 28, 2005 Office Action dated Mar. 28, 2011.

* cited by examiner

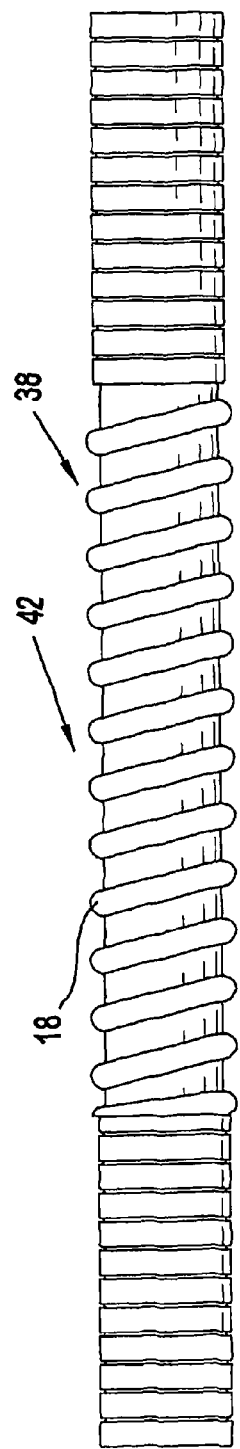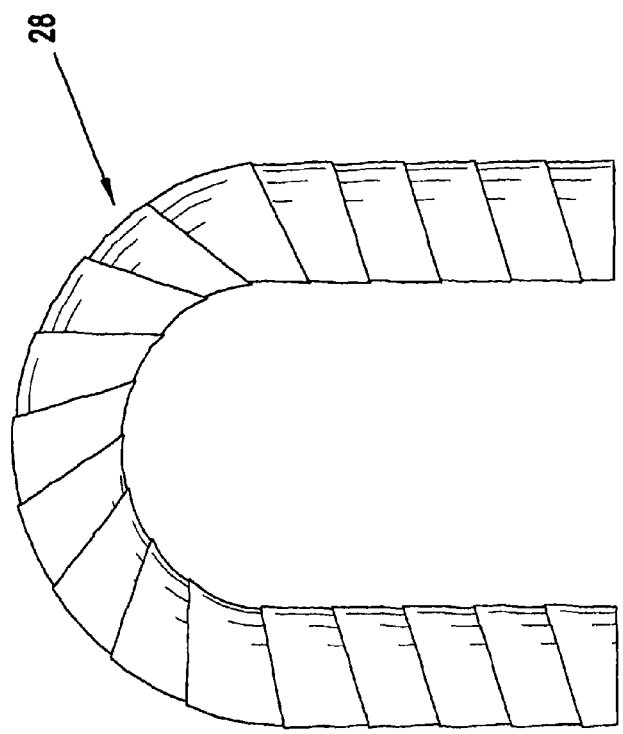
FIG. 8
FIG. 9

KINKED CROSS SECTION
LOSS IN AREA

VASCULAR GRAFT WITH KINK RESISTANCE AFTER CLAMPING

PRIORITY

This application is a U.S. National Stage Application under 35 U.S.C. §371 of International Patent Application No. PCT/US2005/046763, filed Dec. 28, 2005, which is a continuation-in-part application of International Patent Application No. PCT/US2005/031186, filed Aug. 30, 2005, and claims the benefit, under 35 U.S.C. §119(e), to U.S. Provisional Patent Application No. 60/692,172, filed Jun. 17, 2005, each of which is incorporated by reference into this application as if fully set forth herein.

BACKGROUND OF THE INVENTION

Patients suffering from reduced renal function or renal failure often have to undergo hemodialysis treatments. During dialysis, blood is withdrawn from the patient and is circulated through a hemodialysis machine. The machine removes toxic waste products and returns the purified blood to the patient. Typically, dialysis treatments are performed three times a week for the duration of a patient's life unless a kidney transplant procedure occurs. To successfully undergo hemodialysis treatment, blood must be circulated through the hemodialysis machine at 150 to 600 ml/minute or higher flow rate for about 3-4 hours. Blood flow from the venous system is believed to be inadequate to meet the required flow rate and repeated punctures of large arteries are not feasible. Therefore, native fistulas are often created to provide blood flow access for the hemodialysis machines.

If native fistulas are unavailable or cannot be used for hemodialysis, then vascular grafts, typically made from expanded polytetrafluoroethylene (ePTFE) tubes, are surgically placed between an artery and a vein (ePTFE AV grafts). This procedure is especially useful in patients who do not have blood vessels that will support the construction of a more traditional primary native fistula in the forearm. The ePTFE AV grafts, which are extruded, are favored over textile AV grafts, which are woven, knitted, braided or otherwise formed, for several reasons, including the unique microstructure characterized by nodes and fibrils imparted to the ePTFE grafts, which facilitates tissue ingrowth while simultaneously providing a fluid-tight conduit through which blood can flow; and the ability to provide a graft with a relatively thin wall while retaining necessary strength characteristics.

Expanded polytetrafluoroethylene AV grafts are extensively used for hemodialysis treatments as AV bridge fistulae due, at least in part, to the hemocompatibility advantage of the ePTFE material over other materials (such as polyurethane). However, one potential drawback in using ePTFE AV grafts is that they cannot be used safely to withdraw blood for hemodialysis until about 14 days post-implant. This is believed to be due to the non-elastomeric nature of ePTFE, which cannot self-seal upon puncturing. Thus, in the interim, other means of dialysis must be employed (e.g., hemodialysis catheters, etc.). After 14 days, there is typically sufficient tissue ingrowth into the ePTFE surface to act as a sealant layer, and therefore the graft can seal the puncture wound created by removal of the dialysis needle. However, such sealing requires a combination of pressure and hemostasis, which does not lend to uniformity due to the many variables present during such procedures (dialysis technician/nurse skill level, operating conditions, etc.). It is therefore preferable to have a sealing mechanism for an ePTFE vascular graft that is not dependent on hemostasis and the attendant variables associated therewith and which will seal immediately upon implantation so that additional methods of dialysis do not have to be employed.

Accordingly, various sealing techniques, such as placing a layer of elastomeric sealant on ePTFE, and composite structures have been shown or described to provide immediate self-sealing properties to an ePTFE AV graft. Examples of various types of elastomeric sealants, ePTFE grafts, self-sealing grafts, and composite grafts include those disclosed in the following U.S. patents and published applications: U.S. Pat. No. Re. 31,618, U.S. Pat. No. 4,604,762; U.S. Pat. No. 4,619,641; U.S. Pat. No. 4,731,073; U.S. Pat. No. 4,739,013; U.S. Pat. No. 4,743,252; U.S. Pat. No. 4,810,749; U.S. Pat. No. 4,816,339; U.S. Pat. No. 4,857,069; U.S. Pat. No. 4,955,899; U.S. Pat. No. 5,024,671; U.S. Pat. No. 5,061,276; U.S. Pat. No. 5,116,360; U.S. Pat. No. 5,133,742; U.S. Pat. No. 5,152,782; U.S. Pat. No. 5,192,310; U.S. Pat. No. 5,229,431; U.S. Pat. No. 5,354,329; U.S. Pat. No. 5,453,235; U.S. Pat. No. 5,527,353; U.S. Pat. No. 5,556,426; U.S. Pat. No. 5,607,478; U.S. Pat. No. 5,609,624; U.S. Pat. No. 5,620,763; U.S. Pat. No. 5,628,782; U.S. Pat. No. 5,641,373; U.S. Pat. No. 5,665,114; U.S. Pat. No. 5,700,287; U.S. Pat. No. 5,716,395; U.S. Pat. No. 5,716,660; U.S. Pat. No. 5,800,510; U.S. Pat. No. 5,800,512; U.S. Pat. No. 5,824,050; U.S. Pat. No. 5,840,240; U.S. Pat. No. 5,843,173; U.S. Pat. No. 5,851,229; U.S. Pat. No. 5,851,230; U.S. Pat. No. 5,866,217; U.S. Pat. No. 5,897,587; U.S. Pat. No. 5,904,967; U.S. Pat. No. 5,910,168; U.S. Pat. No. 5,931,865; U.S. Pat. No. 5,976,192; U.S. Pat. No. 6,001,125; U.S. Pat. No. 6,036,724; U.S. Pat. No. 6,039,755 U.S. Pat. No. 6,042,666; U.S. Pat. No. 6,056,970; U.S. Pat. No. 6,080,198; U.S. Pat. No. 6,099,557; U.S. Pat. No. 6,203,735 U.S. Pat. No. 6,261,257; U.S. Pat. No. 6,267,834; U.S. Pat. No. 6,287,337; U.S. Pat. No. 6,319,279; U.S. Pat. No. 6,368,347; U.S. Pat. No. 6,416,537; U.S. Pat. No. 6,428,571; U.S. Pat. No. 6,534,084; U.S. Pat. No. 6,547,820; U.S. Pat. No. 6,589,468; U.S. Pat. No. 6,712,919; U.S. Pat. No. 6,716,239; U.S. Pat. No. 6,719,783; U.S. Pat. No. 6,790,226 U.S. Pat. No. 6,814,753; U.S. Pat. No. 6,827,737; U.S. Pat. No. 6,863,686; U.S. Pat. No. 6,926,735; and U.S. Publication Number (US Pub No.) 2003/0004559; US Pub No. 2003/0027775; US Pub No. 2003/0100859; US Pub No. 2003/0139806; US Pub No. 2004/0033364; US Pub No. 2004/0049264; US Pub No. 2004/0054406; US Pub No. 2004/0122507; US Pub No. 2004/0182511; US Pub No. 2004/0193242; and US Pub No. 2004/0215337, each of which is incorporated by reference as if fully set forth herein.

Before accessing an ePTFE AV graft for hemodialysis, a blood flow check through the graft is normally conducted by feeling the pulse through the graft by gently touching the surface of the skin. The ability to feel the pulse through the graft is generally defined as "palpability." Most commercial ePTFE vascular grafts provide good palpability; however, when a layer of elastomeric sealant is placed on the surface of an ePTFE substrate, the palpability of the graft may be compromised if the layer is too thick. Another potential drawback in using ePTFE AV grafts for hemodialysis is that when implanted, there may be a tendency for the graft to form a kink at the loop site. Examples of a typical loop site is shown in FIG. 1A (forearm loop AV graft 2, from the brachial artery to the basilic vein) and 1B (thigh loop AV graft 4, from the femoral artery to the femoral vein). Kinking of the graft at the loop site may occlude blood flow, in which case immediate medical intervention would be required. Clearly, such intervention is strongly disfavored as the likelihood of adverse outcomes are increased. Unfortunately, it has been discovered that ePTFE grafts coated with elastomeric sealant or otherwise formed to address the problem of sealing can easily form kinks, presumably due to the stiffness of the graft at the loop region.

One other potential drawback in utilizing ePTFE material is that it is radially non-compliant compared to a native blood vessel, meaning that the wave propagation of blood, which causes a native blood vessel to expand and contract as pulses of blood flow therethrough, dissipates as it travels through a ePTFE graft. This dissipation of the pulse can lead to various complications, such as compliance mismatch with respect to the host vessel. Unfortunately, to date, it is believed that a radially compliant ePTFE graft that mimics the compliance of a native blood vessel has not been successfully developed. Therefore, there is a need for a self-sealing ePTFE graft that overcomes some or all of the above-mentioned disadvantages.

BRIEF SUMMARY OF THE INVENTION

Accordingly, vascular grafts, and in particular ePTFE grafts and ePTFE AV grafts providing advantageous properties are described herein. In one aspect of the invention, a self-sealing vascular graft includes a generally tubular ePTFE substrate having a first surface and a second surface spaced from the first surface, wherein the ePTFE substrate is selected from the group consisting of a high porosity graft, a thin-wall graft and combinations thereof, and a layer of sealant disposed over one of the first and second surfaces of the substrate. In another aspect of the invention, a self-sealing graft includes a tubular ePTFE substrate, wherein the ePTFE substrate is either a high-porosity graft, a thin-wall graft or a combination thereof, and a layer of sealant disposed over at least a portion of the substrate. In yet another aspect of the invention, a graft for implantation as an AV fistula includes a tubular ePTFE substrate and a layer of sealant disposed over at least a portion of the substrate, wherein the sealant layer has a plurality of grooved sections spaced apart along the length thereof.

In another aspect of the invention, a vascular graft includes an outer polymer sealant layer surrounding a substrate and a base layer, and a plurality of foam layers dispersed between the substrate and the outer polymer layer. According to an alternative aspect of the invention, a vascular graft includes an inner sealant layer of polymer having a first thickness and surrounding a substrate; and a foam layer of polyurethane surrounding the inner sealant layer, the foam layer having a second thickness greater than 1.5 times the first thickness. In still another aspect of the invention, a vascular graft includes a substrate, including an outer wall, a base sealant layer, comprising a polymer sealant material, disposed over a length of the substrate, a first foam layer, comprising a polymer foam material, disposed over a length of the base layer, a beading embedded at least partially in the first foam layer, a second foam layer, comprising a polymer foam material, disposed over a length of the first foam layer and beading, and an outer layer, comprising a polymer.

In an alternative aspect of the invention, a method of forming a radially compliant graft includes providing an ePTFE substrate, radially dilating the substrate, disposing a layer of elastomeric material over the radially dilated substrate to provide a coated substrate, and heating the coated substrate. In another aspect of the invention, a method of forming a vascular graft includes providing an ePTFE substrate, applying a first layer of polyurethane over a length of the substrate, longitudinally compressing the substrate, applying a second layer of polyurethane over the first layer of polyurethane, wrapping a layer of ePTFE tape around the polyurethane coated substrate, the ePTFE tape passing first through a solution such that an amount of solution is applied to the ePTFE tape. In yet another aspect of the invention, a method of making a self-sealing vascular cuff graft includes positioning a neck portion of a cuff over a first end of an ePTFE substrate, dipping the substrate into a sealant material from a second end thereof to the neck portion of the cuff, and dipping the substrate and neck portion of the cuff in the sealant material. In still another aspect of the invention, a method of making a kink resistant self-sealing vascular graft includes providing a generally tubular ePTFE substrate, disposing a layer of sealant over at least a portion of an outer surface of the substrate, and creating grooved sections in the sealant layer.

In a further aspect of the invention, a self-sealing vascular graft includes a generally tubular ePTFE substrate having a first surface and a second surface spaced from the first surface, and a layer of sealant disposed over one of the first and second surfaces, the sealant comprising a polymeric material resistant to plastic deformation upon insertion of a puncture member through the sealant layer. In another aspect of the invention, a self-sealing vascular graft includes a generally tubular ePTFE substrate, a layer of sealant disposed over at least a portion of the substrate, and a beading disposed about a surface of one of the substrate and sealant.

In yet another aspect of the invention, a method of making a kink resistant self-sealing vascular graft includes providing, a generally tubular ePTFE substrate, disposing a layer of sealant over at least a portion of an outer surface of the substrate, positioning a beading over at least a portion of the sealant layer, and coupling a cuff graft to the vascular graft. In another aspect of the invention, a method of making a self-sealing vascular cuff graft includes attaching a beading disposed generally helically about a substantially tubular ePTFE substrate having a first end and a second end extending along a longitudinal axis, coupling a flared vascular cuff to one of the first and second ends, and bonding the coupled vascular cuff and generally tubular ePTFE substrate. In a further aspect of the invention, a method of making a self-sealing vascular graft includes providing an elastomeric sealant layer over a length of an outer surface of an ePTFE substrate, and disposing a foam layer over at least a portion of the sealant layer, wherein a thickness of the foam layer is substantially greater than a thickness of a wall of the substrate. According to another alternative aspect of the invention, a method of making a self-sealing vascular graft includes dispensing at least one layer of polyurethane material onto a surface of an ePTFE substrate, and bonding an ePTFE member to the polyurethane material by applying a solvent to the ePTFE member.

In one embodiment, a self-sealing vascular graft includes a generally tubular ePTFE substrate, including a proximal end section, a distal end section and a central section positioned between the proximal end section and distal end section, at least one of the proximal end section, central section, and distal end section including a self-sealing region, and a first beading contiguous to a surface of the ePTFE substrate along at least a portion of the central section. In another embodiment, a vascular graft includes a generally tubular ePTFE substrate defining a longitudinal axis, a layer of polyurethane matrix disposed about the ePTFE substrate, and a first beading disposed in the polyurethane matrix.

In yet another embodiment, a self-sealing vascular cuff graft includes a generally tubular ePTFE substrate, a self-sealing region extending along a length of the generally tubular substrate between a first and second end thereof, the self-sealing region including at least one of a sealant layer and a foam layer, an outer ePTFE member positioned over at least a portion of the self-sealing region, a first beading positioned over the substrate at the first end adjacent to the self-sealing region, the outer ePTFE member extending over at least a portion of the first beading, a second beading positioned over the outer ePTFE member at the first end adjacent to the self-sealing region, and a flared vascular cuff having a proximal end positioned over at least a portion of the first and second beadings.

In still another embodiment, a vascular graft includes a generally tubular ePTFE substrate defining a longitudinal axis extending through distal portions of the ePTFE substrate, the ePTFE substrate having a first cross-sectional area about the longitudinal axis, and an elastomeric member disposed about the ePTFE substrate so that, as the ePTFE substrate is curved to contact the distal portions of the substrate to a generally circular pin having a diameter of about 20 millimeters or less, the ePTFE includes a second cross-sectional area of the ePTFE substrate of at least about 50% of the first cross-sectional area where the second cross-sectional area is located approximately 20 millimeters from the outer surface of the circular pin.

In one embodiment, a method of making a kink resistant vascular graft includes providing a generally tubular ePTFE substrate, including a proximal end section, a distal end section and a central section positioned between the proximal end section and distal end section, and bonding a first beading to a surface of the ePTFE substrate along at least a portion of the central section.

In another embodiment, a method of making a self-sealing vascular cuff graft includes providing a generally tubular ePTFE substrate, including a self-sealing region extending along a length of the generally tubular substrate between a first and second end thereof, positioning a first beading over the substrate at the first end adjacent to the self-sealing region, disposing an outer ePTFE member over at least a portion of the self-sealing region and the first beading, positioning a second beading over the outer ePTFE member at the first end adjacent to the self-sealing region, and attaching a flared vascular cuff to the substrate over at least a portion of the first and second beadings.

These and other embodiments, features and advantages of the present invention, will become more apparent to those skilled in the art when taken with reference to the following more detailed description of the invention in conjunction with the accompanying drawings that are first briefly described.

BRIEF DESCRIPTION OF THE DRAWINGS

FIG. 8 is an illustration of an ePTFE graft having an ePTFE substrate with a sealant layer on either side of a middle portion, which has beading spiraled therearound, the sealant layer having grooved sections cut in spaced apart intervals therein.

FIG. 9 is an illustration of the graft of FIG. 8 with a foam layer disposed over the sealant layer and beading, shown in a bent configuration.

DETAILED DESCRIPTION OF THE PREFERRED EMBODIMENTS

Figure 1:
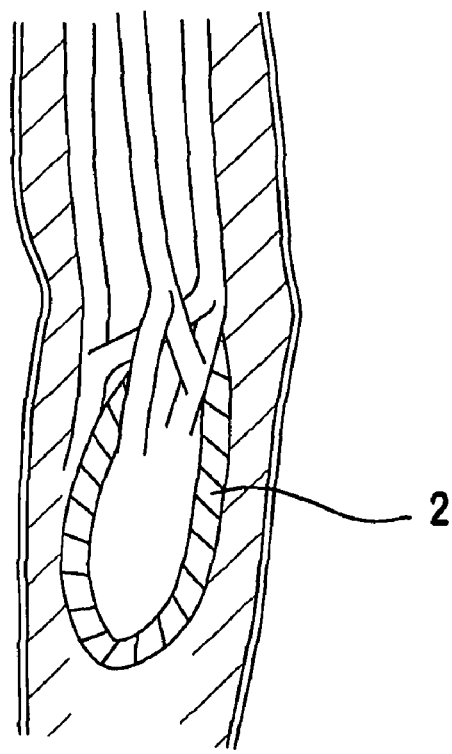
FIG. 1A is a depiction of loop AV graft implanted in the forearm of a patient.
FIG. 1B is a depiction of loop AV graft implanted in the thigh of a patient.
Figure 1:
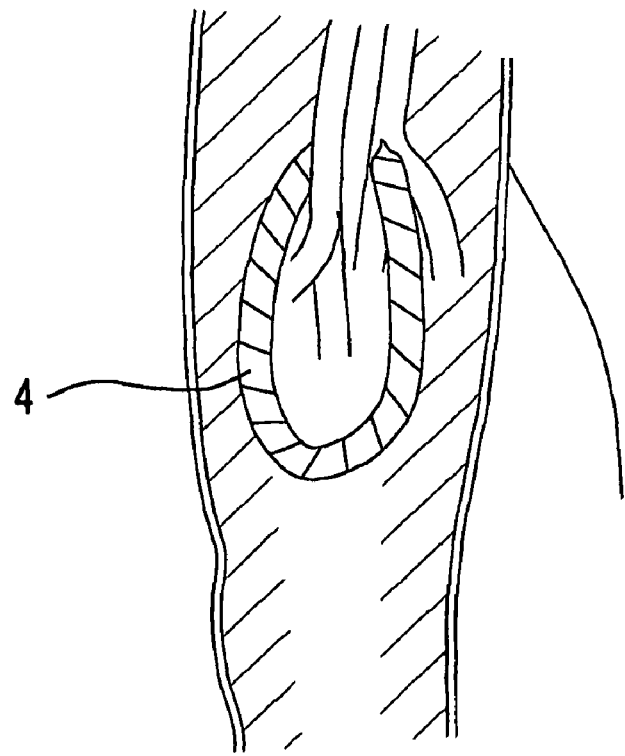

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The examples contained herein utilize an ePTFE substrate. As is known in the art, an ePTFE substrate may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc. While the preferred method used for forming an ePTFE substrate in the present invention is to extrude a tube, it should be appreciated that other forming methods are possible and are within the scope of the invention. Moreover, while ePTFE is discussed as being the material of choice for the substrate layer, one skilled in the art would appreciate that other materials are also suitable for use as a substrate, including, for example, polyester, polyurethane and fluoropolymers, such as perfluoroelastomers and the like.

Further, while the self-sealing properties of the grafts described herein are made with reference to blood loss due to removal of a needle therefrom, it should be appreciated that the self-sealing properties extend to blood loss resulting from suture holes created in the graft during implantation. Further still, it should be appreciated that the discussion of specific polyurethane materials herein with respect to a sealant layer are exemplary only and should not be utilized to limit the invention. In particular, many different types of polyurethane materials are within the scope of the invention, as are non-polyurethane elastomeric sealant materials. As used herein, the terms elastomer, elastomeric, sealant, and the like are used interchangeably to refer to a layer or layers of generally flexible material dispensed or disposed on a substrate that can, in most instances, impart sealing properties thereto but is not required to self-seal upon puncture.

In addition, bioactive agents may be incorporated into the material (or materials) forming the vascular grafts described herein. Bioactive agents can be incorporated with a synthetic non-metallic material (e.g., Dacron, polyester, PTFE, ePTFE, polyurethane, polyurethane-urea, siloxane, and combinations thereof) in at least one of the luminal and abluminal surfaces of the grafts; dispersed throughout the synthetic non-metallic material of the grafts; coated thereon; spray-coated thereon; grafts dipped therein; vapor deposited thereon; sputter-deposited thereon; or used to form radio-opaque surfaces on the grafts. The material or combinations of materials used (e.g., Dacron, polyester, PTFE, ePTFE, polyurethane, polyurethane-urea, siloxane, and combinations thereof) can include surface modifying additives or other materials.

It should be emphasized that variations in the configuration or composition of the substrate, bioactive agents, sealant layers, foam layers, other layers and other design parameters are to be utilized with the graft described herein. For example, the weight percentage of a bioactive agent in the graft can vary from about 0.1 percent to about 90 percent, and most preferably from about 10 to about 60 percent; the average particle size of the bioactive agent may range from about 20 nanometers to about 100 microns, and most preferably from about 0.1 micron to about 5 microns; the bioactive agent particle may be porous in certain configurations and non-porous in other configurations; bioactive agents may constitute 100 percent of the luminal or abluminal surface of the graft and can be homogeneously distributed throughout the entire graft body; bioactive agents may also constitute an adhesive film of about 10 microns to about 1000 microns.

Bioactive agents may include, but are not limited to, compounds such as carbon particles, silver particles, graphite particles, antibiotics (amethoprinrifampin or gentamycin); macrolide antibiotics; steroidal or anti-inflammation agents (e.g., estradiol); antineoplastic agents; antifungals; antivirals; antibodies; genetic sequence agents; growth factors inhibitors; angiogenesis; anti-angiogenesis; proteinase inhibitors; antiproliferative compounds or cell cycle modulators (such as rapamycin, sirolimus, or paclitaxel. Other bio-active agents can also include, but are not limited to agents such as, for example, anti-proliferative/antimitotic agents including natural products such as vinca alkaloids (i.e. vinblastine, vincristine, and vinorelbine), paclitaxel, epipidophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

These agents may be coupled with other agents, such as hydroxyapatite (HA), or other bio-compatible calcium salts, including, but not limited to dicalcium phosphate, tricalcium phosphate, tetracalcium phosphate, and other compounds in the calcium phosphate or calcium carbonate family. Any of the member of the family of calcium salts described can be utilized as long as the salt is not substantially osteo-inductive (i.e., bone forming) in the graft. Also, ceramic materials such as nano-sized carbon tubes, calcium carbonate, and genetic or viral materials may also be combined with at least one of the graft materials described herein.

With respect to utilization of HA or other bio-compatible calcium salts, various methods or techniques known to those skilled in the art can be used to incorporate drugs or bioactive compounds therein. For example, drugs may be added after a HA-graft composite is made. Organic or aqueous solvent based techniques can be used to diffuse the drugs or other bioactive agents into the HA particles. Alternatively, HA particles may be first loaded with drugs or other bioactive agents and then incorporated in the graft. The drug or other bioactive agent may be released quickly within 60 minutes or can be released in a controlled manner from few days to two years. Additional polymeric coating or ceramic coating on HA particles may be used to control the release of the drug or other bioactive agent.

Additionally, where ePTFE is used in conjunction with HA, the composite HA-ePTFE grafts may have different porosities and node-fibril structures. Porosity of the ePTFE may be in the range of about 5 microns to about 100 microns, with the preferred porosity or internodal distance ranging from about 10 microns to about 40 microns. By controlling expansion ratios, lubricant levels, PTFE resin particle size and other ePTFE processing parameters, grafts with various porosities can be made to provide HA coupled grafts with regions of different porosities. The HA coupled graft may also be made using multiple layers of ePTFE graft tubes. The HA based grafts may also have additional features described herein, such as a cuff or cuffs to improve patency, beading to improve kink resistance, and visible orientation lines to assist during implantation or other surgical procedures. These and other aspects of grafts incorporating HA or other bio-compatible calcium salts are described in U.S. Provisional Application No. 60/689,034, filed Jun. 8, 2005, entitled "Grafts and stent grafts having inorganic bio-compatible calcium salt," which is incorporated by reference as if fully set forth herein.

Sealant Layer

In one preferred embodiment of a self-sealing graft, the sealant layer material utilized is one that is believed to exhibit a low degree of creep or stress relaxation. Creep or stress relaxation of a material occurs due to plastic deformation thereof, which in the context of the preferred embodiments may occur due to the insertion of a needle through the material for an extended length of time. Examples of suitable materials for the sealant layer include, but are not limited to, aromatic polycarbonate polyurethanes, polyetherurethanes, polyether/polyamide block copolymers, polydimethylsiloxane elastomers, other silicone elastomers, etc. In particular, preferred polyurethanes that exhibit a low degree of creep or stress relaxation include aromatic polyurethanes. Further, the sealing response of the sealant layer may be improved through manipulation of the polymer by heating, which results in the lowering of the creep or stress relaxation exhibited by the sealant layer and/or by adding particles including polyethylene terephthalate (polyester) to the sealant material, as described in detail in PCT/US05/31186, filed Aug. 30, 2005, entitled "Self-Sealing PTFE Graft with Kink Resistance," which is incorporated by reference as if fully set forth herein. It is also noted that the thickness of the sealant will impact the sealing response of the graft, and that graft characteristics can be manipulated through the changing of the thickness of the sealant, which may be in addition to the processes/methods discussed above with respect to improving the sealing response of the graft (i.e., type of sealant chosen, heating processes, particle addition, etc.).

Self-Sealing ePTFE Graft

A self-sealing graft as described herein includes an ePTFE substrate with a sealant layer thereon, as described in U.S. Pat. No. 5,152,782 to Kowligi et al., which is commonly assigned and is incorporated by reference as if fully set forth herein. In particular, ePTFE substrates that are classified to one skilled in the art as either a high porosity graft or a thin-wall graft have been coated with a sealant layer and compared with a regular wall graft with a sealant layer, as well as the aforementioned types of grafts without a sealant layer. The term "high porosity graft" as used herein means a graft having an internodal distance (IND) in the range from approximately 30 to approximately 100 microns. The term "thin-wall graft" as used herein means a graft having a wall thickness less than approximately 500 microns, more preferably thickness ranging from approximately 200 to approximately 500 microns. By providing an ePTFE substrate that is either a thin wall graft or a high porosity graft (or a combination thereof), a sealant layer (e.g., elastomeric sealant such as polyurethane) disposed thereon such that it adequately penetrates into the wall of the ePTFE substrate will tend to dominate the closure response upon needle removal, as described in detail in PCT/US05/31186, filed Aug. 30, 2005, entitled "Self-Sealing PTFE Graft with Kink Resistance," which is incorporated by reference as if fully set forth herein.

ePTFE AV Graft

An ePTFE graft coated with a sealant, in addition to exhibiting advantageous self-sealing properties, may have the accompanying disadvantage of considerably lowering the kink resistance of the graft. Thus, embodiments of an ePTFE substrate coated with only a sealant layer may be favored in the case that an ePTFE AV graft is implanted in such way that no bend in the graft is necessary. Where an ePTFE AV graft will require a bend for implantation (such as shown in the examples of FIGS. 1A and B), additional processing steps may be required to impart kink resistance to the graft.

A first example of a processing step to increase kink resistance in a coated ePTFE graft, which step also imparts longitudinal compliance to the graft, is a step of longitudinally compressing the ePTFE graft prior to the step of coating the ePTFE graft with a sealant, as shown and described in U.S. Pat. No. 4,995,899 to Della Corna et al., which is commonly assigned and is incorporated by reference as if fully set forth herein. Compression of the ePTFE graft can be accomplished, for example, by placing the ePTFE graft over a cylindrical mandrel and applying a compression force along its longitudinal axis. The compression of the ePTFE graft prior to coating acts to increase kink-resistance by allowing the graft to stretch on the outer diameter of the bend and compress on the inner diameter of the bend. For ePTFE AV grafts, the longitudinal compression of the ePTFE graft prior to coating with a sealant layer is generally utilized whether or not further processing steps are employed.

A second example of a processing step to increase kink resistance in a coated ePTFE graft is a step of wrapping a beading around the outer surface of the graft. Depending on the specifications of the coated ePTFE graft over which the beading will be disposed (e.g., material properties of graft, dimensions of graft, material properties of sealant, dimensions of sealant layer, intended use of the graft, intended placement location of the graft, etc.), a number of beading parameters are possible. For example, the thickness of the beading, the type of beading material, the hardness of the beading, the spacing between windings of the beading, the cross-sectional shape of the beading, and the winding angle of the beading can all be varied to achieve the intended performance of the ePTFE AV graft, and in particular the kink resistance thereof. Further, a radiopaque pigment can be incorporated into the beading to provide radiopacity for X-ray contrast. Examples of radiopaque materials to be incorporated into the beading include, but are not limited to, barium sulfate, bismuth subcarbonate, bismuth trioxide, tungsten, tantalum, etc. In one embodiment, the beading includes a metallic material exhibiting radiopacity. Although a beading has been illustrated as an elongated member wrapped about the ePTFE, it should be noted that the beading includes distinct elongated members wrapped about the ePTFE as separate members (e.g., a plurality of rings) or connected to each other directly or through an intermediate member.

A third example of a processing step to increase kink resistance in a coated ePTFE graft is a step of selective deposition of sealant materials on the graft surface. Such selective deposition can be accomplished by sectioned laser ablation or otherwise grooving the sealant material at spaced apart intervals over at least a portion of the length of the coated ePTFE graft. The grooving can be accomplished through the use of a $CO_2$ laser or other instrument that is capable of cutting precision grooves through the sealant layer to the ePTFE substrate. The grooves can be cut into the sealant layer at any angle or depth and can be spaced apart at any length. Moreover, the angle of the grooves and/or the length between grooves can be varied along selected lengths. The grooving of the coated ePTFE graft as a processing step can be used either alone or in combination with the previously mentioned processing steps and/or any processing steps not specifically mentioned herein to increase kink resistance in a coated ePTFE graft. In addition, only selected lengths of the coated ePTFE graft may be grooved (e.g., a mid-portion of the coated ePTFE graft where the graft is to be bent upon implantation).

A fourth example of a processing step to increase kink resistance in a coated ePTFE graft is a step of placing a foam layer over the coated ePTFE graft. The foam can include a polymer material and may be disposed onto the outer surface of a coated ePTFE graft (which may have undergone any of the above-referenced processing steps either alone or in combination). Examples of ways in which a polymer foam may be disposed onto the outer surface of a coated ePTFE graft are provided in detail in PCT/US05/31186, filed Aug. 30, 2005, entitled "Self-Sealing PTFE Graft with Kink Resistance," which is incorporated by reference as if fully set forth herein.

A coated ePTFE graft may further be prepared for use as an ePTFE AV graft by wrapping with an outer layer of porous material, such as ePTFE tape. The addition of an outer wrap is believed to enhance tissue ingrowth into the ePTFE AV graft to anchor the graft within the body tissue and also to reduce tissue fluid exposure to the polyurethane layer(s). The thickness and density of the outer wrap can be selected so that kink resistance and handling are not negatively affected. With respect to adhering ePTFE tape to an underlying non-PTFE material, such as polyurethane, it has been discovered that concomitant use of a solvent, such as THF, acts to bond the ePTFE tape to the underlying material. The THF or other solvent can be applied to the ePTFE tape by spraying after the tape has been applied to the graft (i.e., helically wrapped) or by soaking the tape in the solvent prior to wrapping.

In a preferred embodiment, ePTFE tape is wrapped over a sealant layer, such as polyurethane, after first passing over or through a solvent dispensing apparatus. For example, a graft on a mandrel could be rotated as ePTFE tape is fed from a spool on a pulley system, the ePTFE tape passing over a dispensing apparatus positioned between the mandrel and pulley system. The dispensing apparatus could take on a variety of configurations, but in one embodiment is a pressurized tube with one or more apertures, slits or other openings therein connected to a reservoir containing the solvent to be dispensed, a pressure control device and a regulator. Positioned over the opening(s) on the dispensing tube is a sponge or similarly functioning article that becomes saturated with the solvent upon commencement of the procedure. As the ePTFE tape is fed from a spool on the pulley system to the graft on the mandrel, it passes over the dispensing tube sponge, such that an even amount of solvent is applied to the ePTFE tape.

Figure 2:
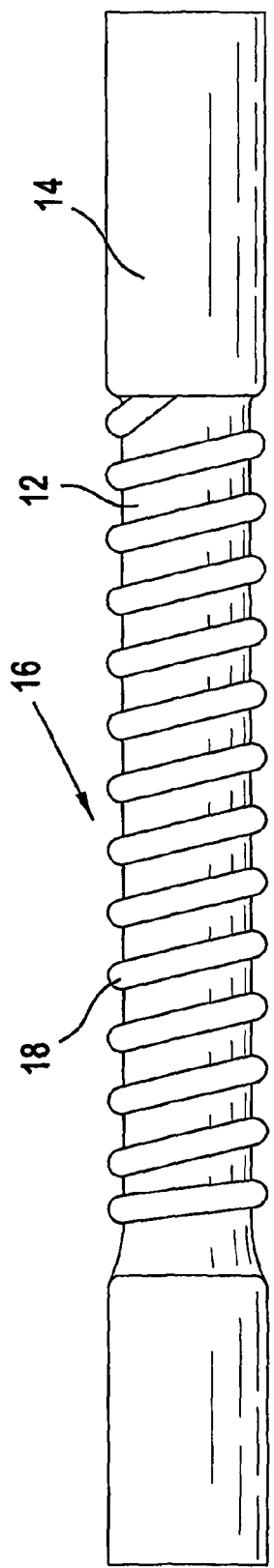
FIG. 2 is an illustration of an ePTFE graft having an ePTFE substrate with a sealant layer on either side of a middle portion, which has beading spiraled therearound.
Figure 3:
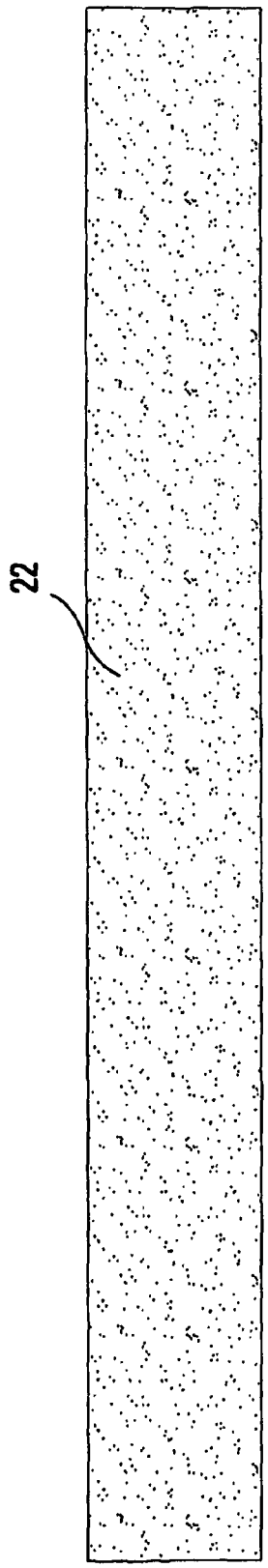
FIG. 3 is an illustration of the graft of FIG. 2 with a foam layer disposed over the sealant layer and beading.
Figure 4:
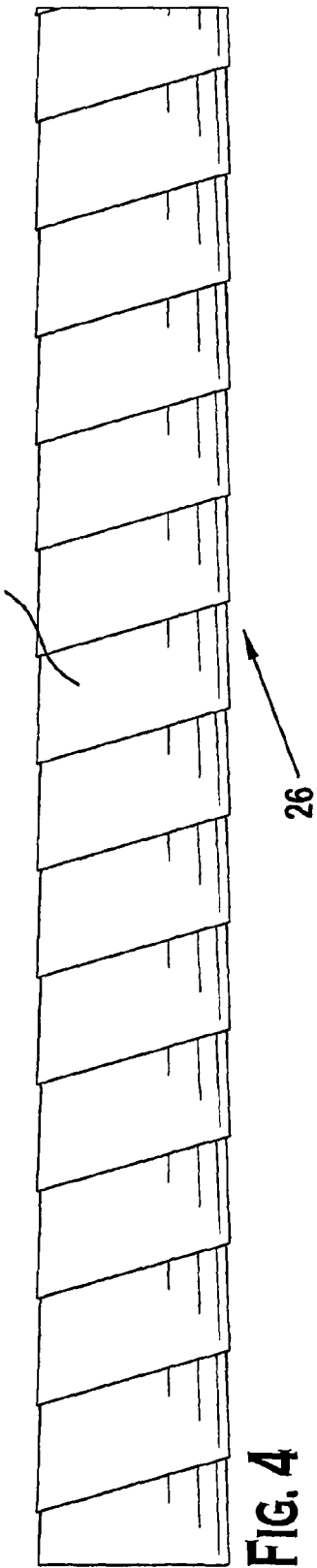
FIG. 4 is an illustration of the graft of FIG. 3 with an ePTFE tape wrapped around the foam layer.
Figure 5:
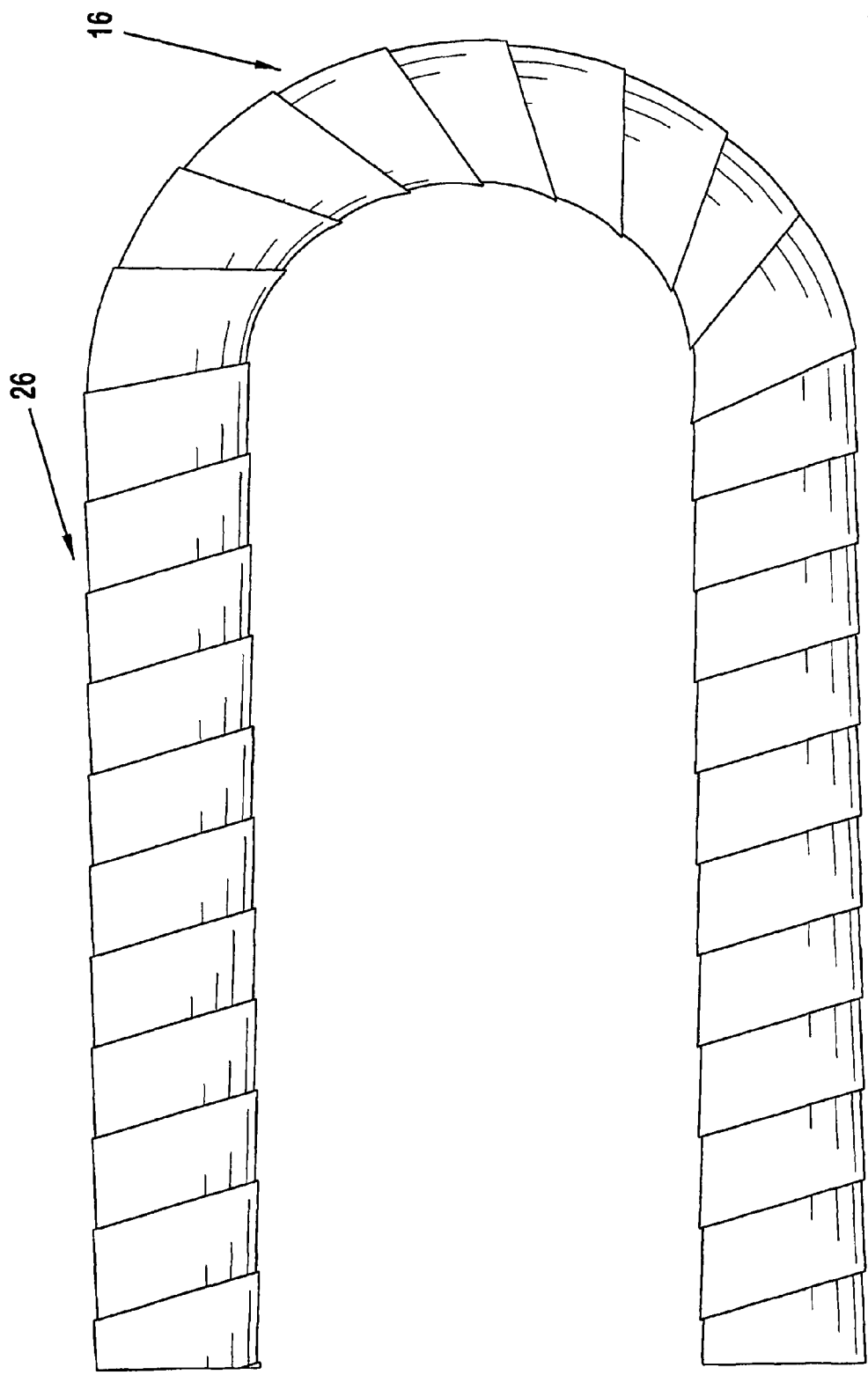
FIG. 5 is an illustration of the graft of FIG. 4 shown in a bent configuration.
Figure 6:
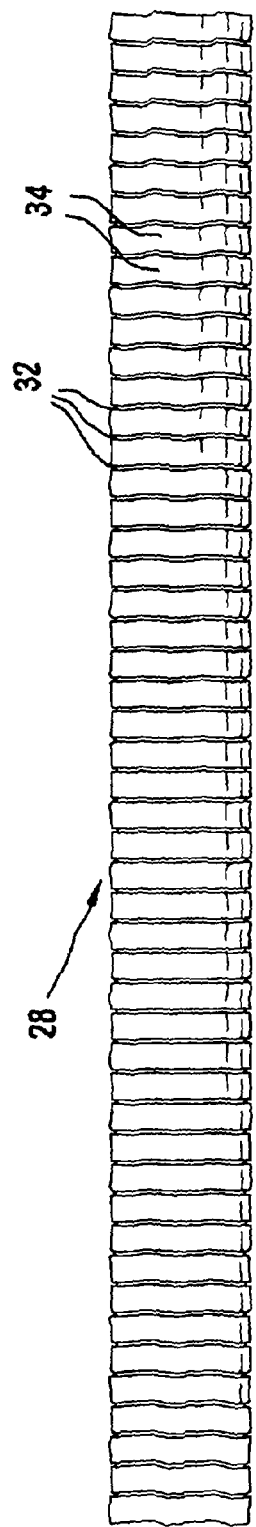
FIG. 6 is an illustration of an ePTFE graft having an ePTFE substrate with a sealant layer over its length, the sealant layer having grooved sections cut in spaced apart intervals therein.
Figure 7:
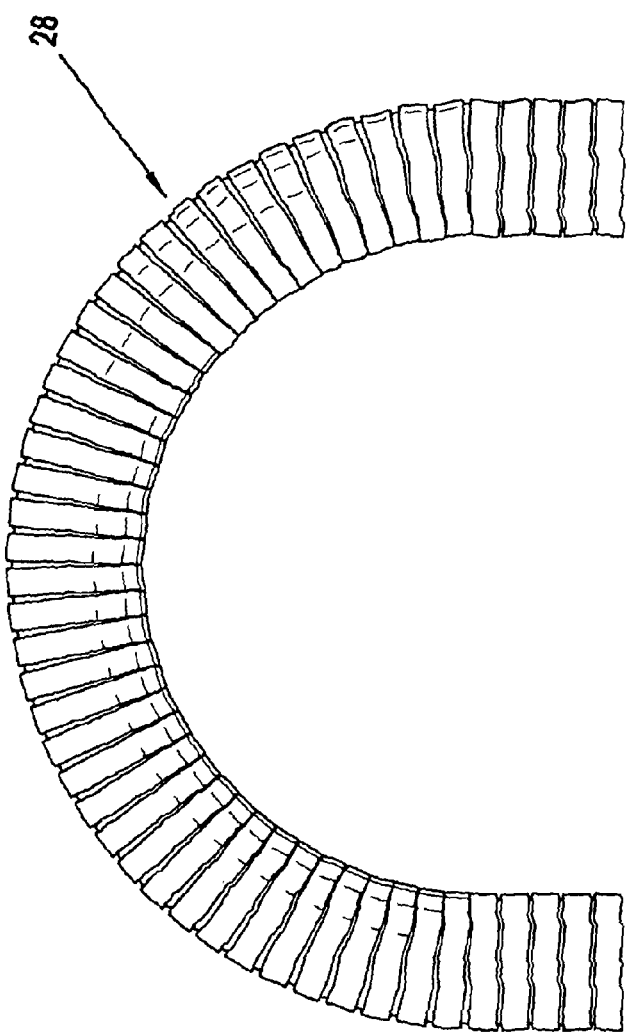
FIG. 7 is an illustration of the graft of FIG. 6 shown in a bent configuration.

FIGS. 2-9 are illustrations of coated ePTFE grafts incorporating one or more of the above-identified processing steps. FIG. 2 shows an ePTFE substrate 12 having a polyurethane coating 14 over portions of its length leading up to a middle portion 16, but not including the middle portion 16, which has a helically wrapped PTFE beading 18 disposed thereon. FIG. 3 shows a polymer foam layer 22 over the ePTFE graft of FIG. 2, while FIG. 4 shows an outer wrap of ePTFE tape layer 24 helically wound about the foam layer 22 of FIG. 3 to create an ePTFE AV graft 26. FIG. 5 shows the graft 26 of FIG. 4 in a looped configuration (i.e., bent along middle portion 16), exhibiting excellent kink resistance at a very small radius. FIG. 6 shows a graft 28 including an ePTFE substrate having a polyurethane coating over its entire length, the coating having grooves 32 cut therein at an angle approximately perpendicular to the longitudinal axis of the graft. The graft 28 also has a pair of parallel orientation lines extending longitudinally along a length thereof. FIG. 7 shows the graft 28 of FIG. 6 in a looped configuration to demonstrate the kink resistance provided by the grooves 32. FIG. 8 shows a graft 38, similar to graft 28, but without any sealant layer on a middle portion 42, which instead includes a helically wrapped PTFE beading 18 (as in FIG. 2). FIG. 9 shows graft 38 with a foam layer 44 in a looped configuration, also exhibiting excellent kink resistance at a very small radius.

Figure 10:
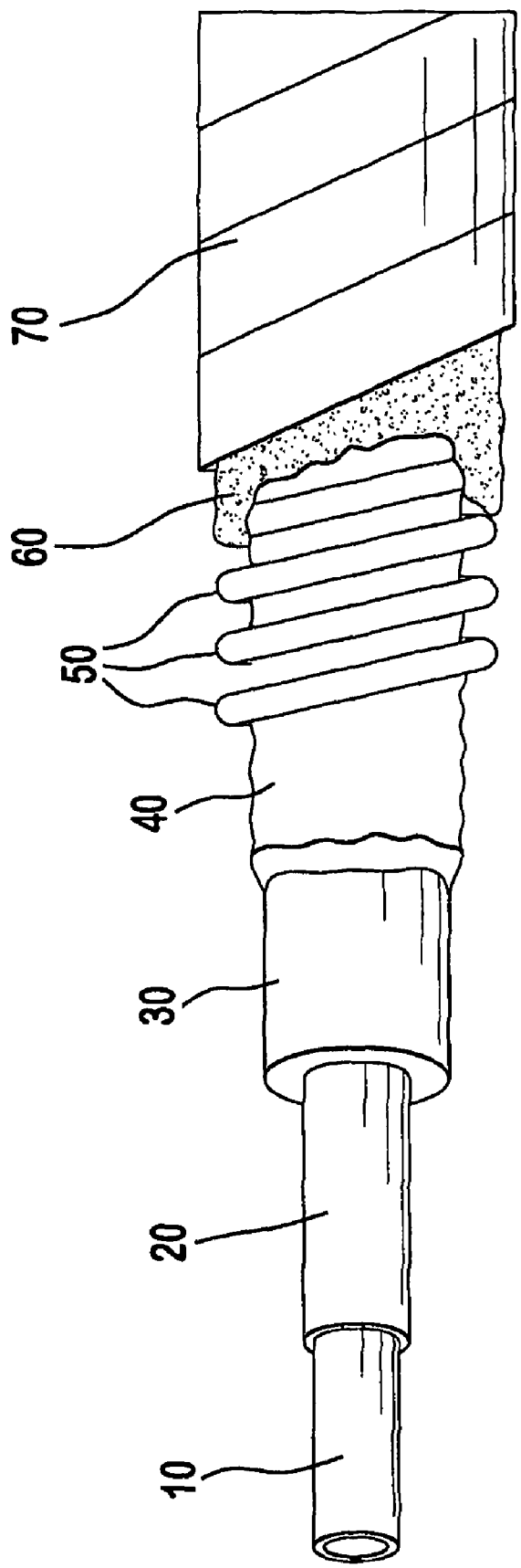
FIG. 10 is an illustration of an ePTFE AV graft according to the present invention with multiple layers of material.

FIG. 10 illustrates different layers of material for an ePTFE AV graft as described herein. It should be appreciated that the disposition of the layers in FIG. 10 is to exemplify the different types of layers and does not necessarily reflect the order of the layers with respect to one another. An ePTFE tubular substrate 10, which may include a thin-wall graft or high porosity graft as discussed above, is surrounded by a polyurethane base coat 20. This base coat 20, which in one embodiment is disposed over the entire length of the ePTFE substrate 10, may be made of a material such as polyurethane. A portion of the base coat will penetrate the wall of the graft. A sealant layer 30 is disposed over the base coat 20 and also may be made of polyurethane (or other types of materials, as discussed above), having a thickness which is dependent on various factors such as graft wall thickness, sealant type, etc. Generally, however, the thickness of the sealant layer and base coat will be in the range of approximately 10-400 microns, preferably about 20 microns to about 40 microns for the base coat 20, and about 100 microns total for the sealant layer and base coat. The sealant layer 30 may be disposed over the entire length of the graft, but in one embodiment is not positioned over either the ends of the graft nor in a middle portion of the graft. As discussed above, the sealant layer 30 may be grooved along selected lengths of the graft to aid in kink resistance. Positioned over the sealant layer 30 is a foam layer 40, followed by a beading layer 50, another foam layer 60 and an outer wrap layer 70.

Figure 11:
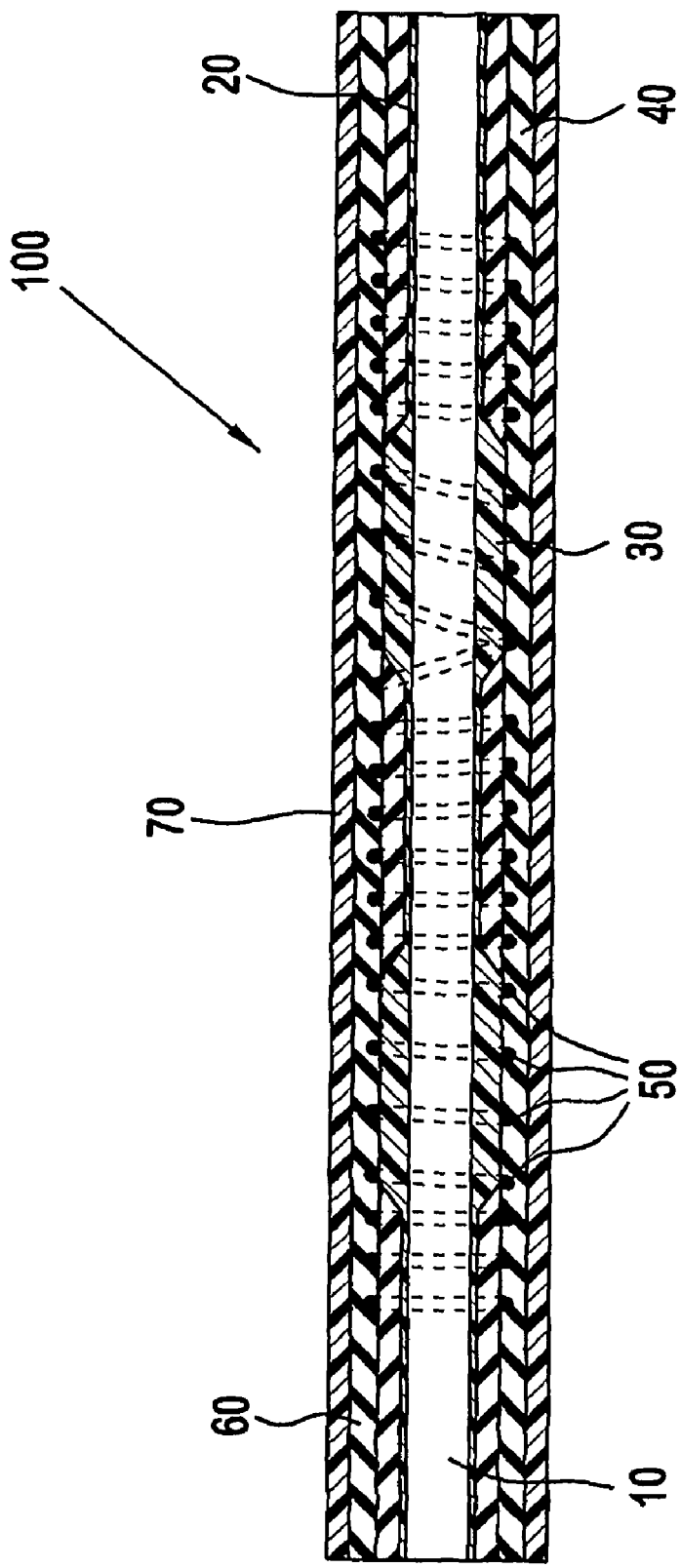
FIG. 11 is an illustration of one embodiment of an ePTFE AV graft according to the present invention.
Figure 12:
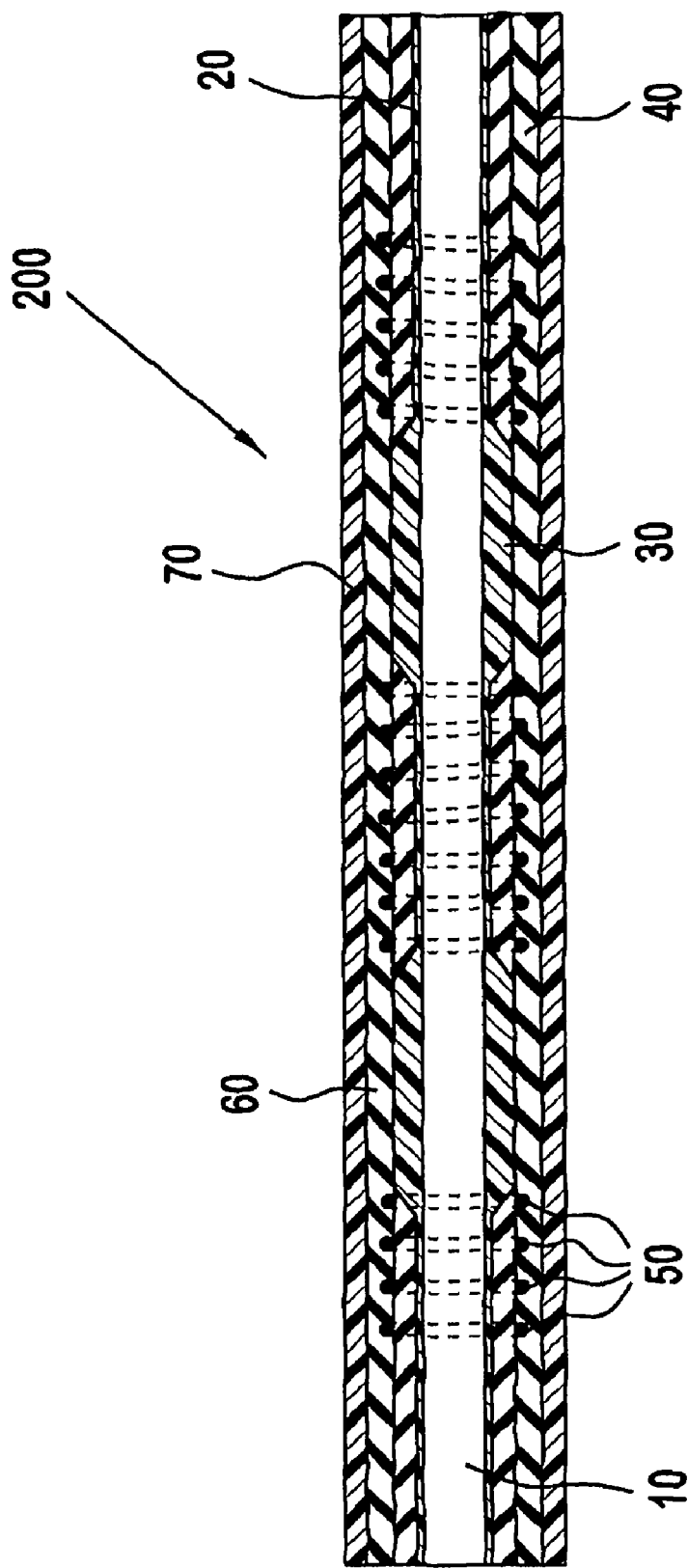
FIG. 12 is an illustration of another embodiment of an ePTFE AV graft according to the present invention.

FIGS. 11-14 illustrate examples of other preferred embodiments of an ePTFE AV graft, each of which incorporate some or all of the layers described in FIG. 10. FIG. 11 is a cross-sectional depiction of an ePTFE AV graft 100, in which an ePTFE substrate 10 is coated along its length by a base layer 20. On top of the base layer 20 at axially spaced apart locations is a sealant layer 30, a foam layer 40 being disposed over the sealant layer 30 such that the foam layer 40 comes in contact with the base layer 20 in areas substantially devoid of the sealant layer 30. Over the foam layer 40, beading is spiraled around a middle portion of the graft 100, creating a beading layer 50 and another foam layer 60 is applied. Around the foam layer 60, a wrap layer 70 is positioned by wrapping a material such as ePTFE tape (as discussed above), which can be wrapped helically. FIG. 12 is a cross-sectional depiction of an ePTFE AV graft 200, which is similar to ePTFE AV graft 100, the difference being that the beading layer 50 includes beading spiraled over spaced apart lengths of a middle portion of the graft 200 such that the beading is positioned in the locations where gaps are present in the sealant layer 30 (i.e., the beading does not overlap lengths of the graft 200 that contain sealant 30). One advantage of this embodiment is the ability to allow a surgeon to unwind the beading of the graft from one end to any desired length in order to allow for suturing of the graft end in an anastomosis, while preserving the kink-resistance of the graft right up to the anastomosis.

Figure 13:
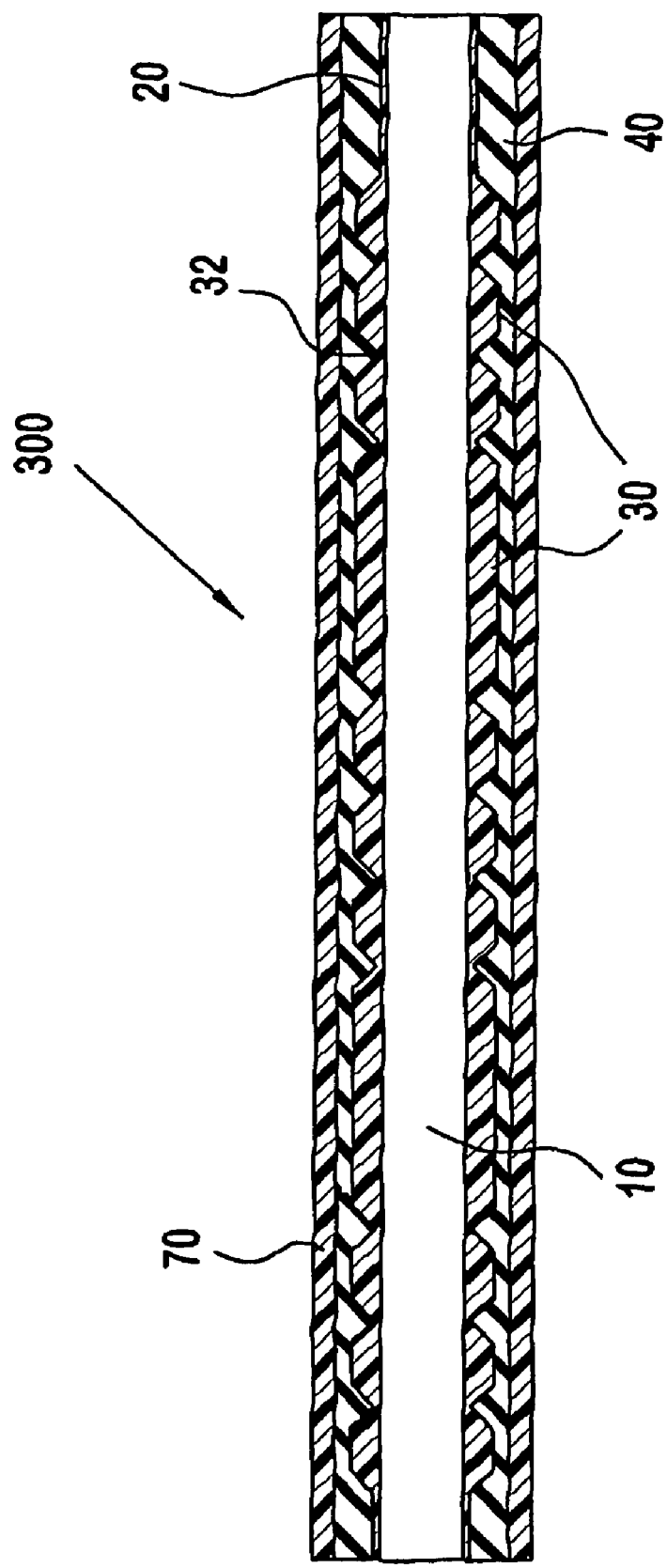
FIG. 13 is an illustration of yet another embodiment of an ePTFE AV graft according to the present invention.
Figure 14:
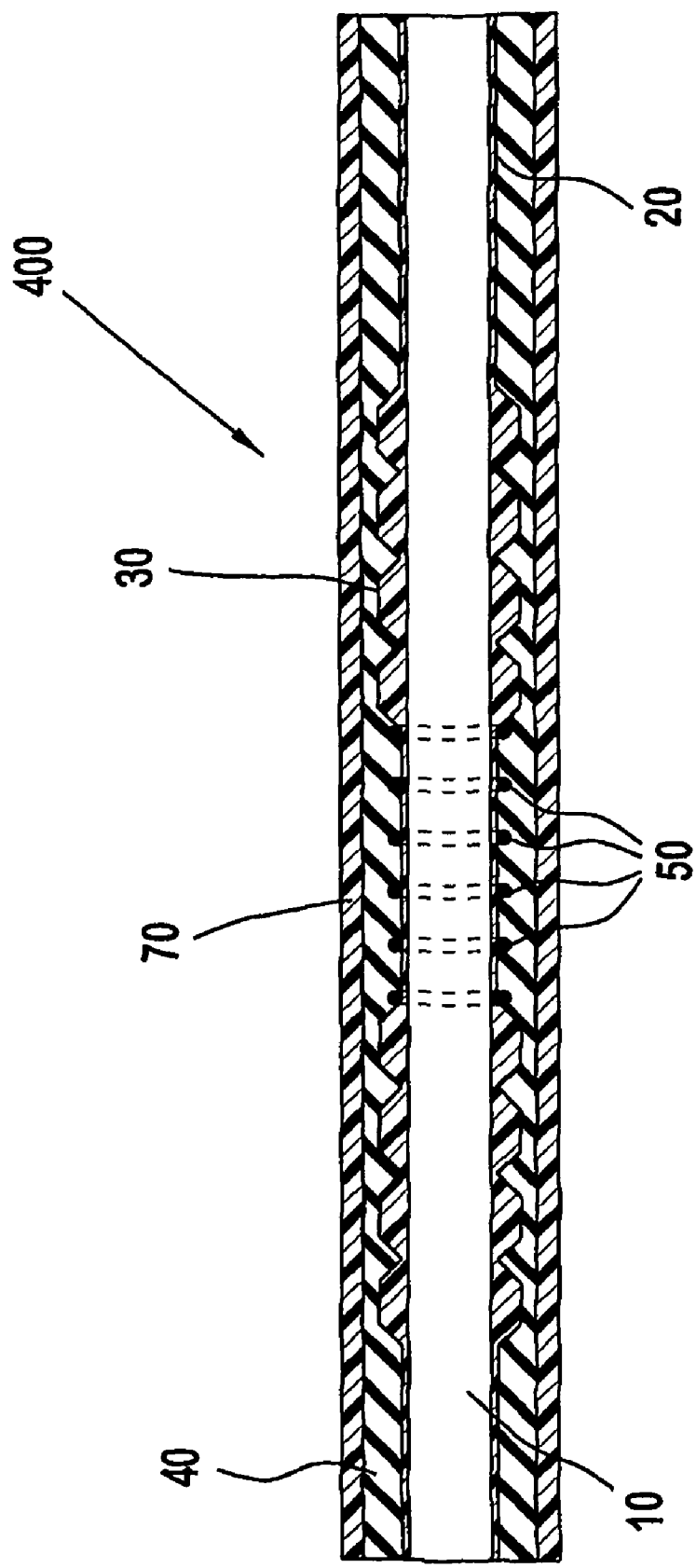
FIG. 14 is an illustration of still another embodiment of an ePTFE AV graft according to the present invention.
Figure 15:
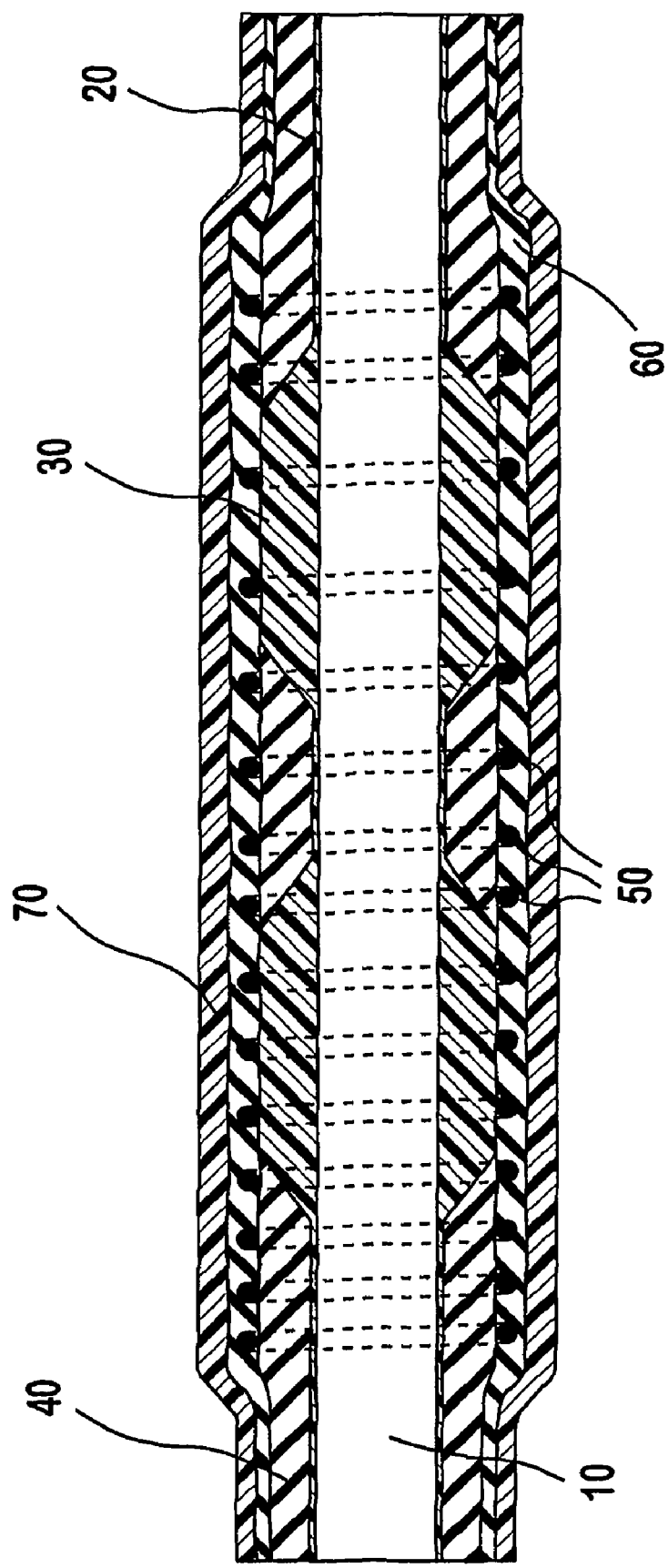
FIG. 15 is an illustration of another ePTFE AV graft according to the present invention.

FIG. 13 is a cross-sectional depiction of an ePTFE AV graft 300, having a base layer 20 over an ePTFE substrate 10. In this embodiment, the sealant layer 30 positioned over the base layer 20 is continuous along a middle portion of the graft 300 with "V" shape grooved sections 32 cut down to the base layer 20. As illustrated, the grooved sections 32 are spaced apart in three small intervals followed by one long interval. Such intervals, however, could be patterned in numerous different ways to achieve desired flexibility and kink-resistance for the graft 300. A foam layer 40 is disposed over the sealant layer 30, followed by a wrap layer 70. FIG. 14 is a cross-sectional depiction of an ePTFE AV graft, having a sealant layer 30 similar to that of FIG. 13, but in place of the long interval of sealant 30 in a middle portion of the graft 300, a beading layer 50 is positioned in a middle portion of the graft 400.

It should be appreciated that each of the above-described grafts may also incorporate one or more longitudinal orientation lines (e.g., one or more blue stripes) along an outer surface thereof to ensure proper alignment (no twisting) during implantation. The orientation line or lines may also assist during manufacture to ensure that the graft is not twisted when mounted on a rotating mandrel or the like (to avoid, for example, a graft with non-homogeneous characteristics). For example, the ePTFE substrate for the self-sealing vascular grafts discussed herein may be manufactured with one or more colored (e.g., black, blue, etc.) lines so that the alignment of the line on the mandrel onto which the substrate is placed (e.g., for further processing steps in building a self-sealing vascular graft) provides visual confirmation to the manufacturer that the graft is not twisted. The orientation line or lines may be incorporated onto the substrate using a standard co-extrusion process. The preferred orientation line or lines are made from a black, blue or green biocompatible pigment or dye. The most preferred color is blue. With respect to the one or more orientation lines incorporated onto the outer surface of a self-sealing vascular graft, a printing process can be performed. The line or lines on the substrate or outer surface of the graft may be solid lines, dashed lines, or a combination thereof to indicate the center of the graft or to indicate different regions (such as cannulation regions) of the graft. It should also be noted that, instead of a line or lines, an alphanumeric identifier or a combination of line(s) and alphanumeric identifier(s) may be printed or otherwise disposed on the ePTFE surface.

In the event that the outer surface of the self-sealing vascular graft includes ePTFE, special ink compositions are necessary to ensure adherence of the line or lines on the ePTFE surface. In one embodiment, an ink composition for an orientation line for an ePTFE surface includes a suitable polymeric binder that adheres well to an ePTFE surface, a biocompatible dye or pigment, and a solvent that dissolves a polymeric binder. In addition, the ink composition may contain inorganic white solid materials such as titanium dioxide (to adjust ink shade) and a viscosity modifier. Although many pigments or dyes may be used to make the orientation line, pigments or dyes that have a long history of human implantation are most preferred. The preferred color compounds in the ink include, but are not limited to: (Phthalocyaninato(2-)) copper, D&C Blue No. 9, D&C Green No. 5, Chlorophyllin-copper complex, oil soluble, Chromium-cobalt-aluminum oxide, Ferric ammonium citrate, D&C Blue No. 5, FD&C Blue No. 2, D&C Green No. 6, Titanium dioxide, carbon, Iron oxide, and the like. (Phthalocyaninato(2-)) copper is the most preferred blue compound. The color of the ink (e.g., black, blue, etc.) may be determined by viewing under a light having a temperature of about 6500 degrees Kelvin.

One preferred example of an ePTFE AV graft produced according to the description provided is now described. An ePTFE substrate with a carbon lined inner surface is extruded with an orientation line (also made of carbon) and longitudinally expanded such that the final internodal distance (IND) is from about 10 microns to about 40 microns and the wall thickness is from about 200 microns to about 300 microns, preferably about 260 microns. The ePTFE substrate is positioned over a mandrel (e.g., having a diameter of about 6.3 mm) and the mandrel is rotated as two passes of a polycarbonate polyurethane are applied. The polyurethane is applied using a Binks Model 2001 spray gun with a nozzle orifice diameter less than about 1 mm, the polyurethane and a solvent, such as THF, (with non-oxidizer type inhibitor) being pressurized from the top of the spray gun and mixing with ambient air (although in one embodiment nitrogen is used in place of air) when the polyurethane is sprayed from the nozzle of the spray gun. The spray gun is spaced from the ePTFE substrate from about 2 inches to about 15 inches, preferably less than about 3 inches, while the polyurethane is sprayed onto the substrate. In the first pass, the mandrel is rotated from about 150 rpm to about 260 rpm, while in the second pass, the mandrel is rotated from about 350 rpm to about 675 rpm, preferably about 435 rpm. This forms a sealant layer or coating on the graft, having a thickness of preferably about 100 microns.

The first pass of polyurethane, which is initially dissolved in solvent as described above until a desired viscosity has been achieved (the length of the polyurethane strands varies with the viscosity—higher viscosity results in longer strands), is applied to the outer wall of the substrate (with some polyurethane penetrating into the outer wall) until a base coat of polyurethane has been applied, having a thickness of about 20 microns to about 40 microns. It should be noted that in some circumstances, the polyurethane, such as polycarbonate polyurethane, should first be heated in order for it to dissolve in the solvent. The resulting structure (substrate and first pass of polyurethane) is then longitudinally compressed (e.g., by hand) and the second pass is applied, in which additional coats of polyurethane are applied over the substrate and base coat of polyurethane in the same manner (but with faster rotation of the mandrel) until the total thickness of the polyurethane sealant layer is about 100 microns (a laser micrometer is used to verify thickness).

A polyurethane foam layer is then applied over the polyurethane sealant layer, having a thickness of about 700 microns, such that the total wall thickness of the graft structure following the application of the foam layer is from about 1 mm to about 1.1 mm. In a preferred embodiment, the foam layer has a thickness equal to the thickness of the ePTFE substrate, or in a more preferred embodiment, the foam layer has a thickness two times the thickness of the ePTFE substrate, and in a most preferred embodiment, the foam layer has a thickness greater than two times the thickness of the ePTFE substrate. The foam layer is applied by spraying polycarbonate polyurethane onto the sealant layer at a distance of about 12-20 inches and preferably at a distance of about 15 inches. Following application of the foam layer, the graft structure is placed in an oven set at an air temperature of about 50° C. to about 70° C. for about 1 hour to about 24 hours, preferably about 50° C. air temperature for about 15 hours, to cure (i.e., to re-establish the hydrogen bonds that were broken down), after which, a beading of polyurethane with barium sulfate (which provides radiopacity for visualization) is helically wrapped over the cured graft structure. The beading can have a variety of cross-sectional shapes, including round, oval, etc., but in a preferred embodiment the beading has a rectangular shape.

More specifically, in a preferred embodiment the beading is made of Carbothane® PC-35 (hardness of 72 Shore D) with 20% barium sulfate filler (to increase rigidity), supplied by Polymer Engineering Group, Tempe, Ariz., having a rectangular cross-sectional shape in which the longer side is about 1 mm and the shorter side is about 500 microns, the longer side being positioned against the outer surface of the graft. In a preferred method of applying the beading to a graft, the beading is preloaded by placing under tension of about 500 grams of force as it is wound through a solution of solvent and about an outer surface of the graft with adjacent windings of the beading being spaced from about 1 mm to about 2 mm apart. The wrapping is done under tension so that the beading becomes embedded into the foam layer. Next, another foam layer is applied, resulting in an overall wall thickness from about 1 mm to about 5 mm, and most preferably, the bead spacing over the area to be cannulated is about 4 mm and the center flex beading is about 2 mm. Over this foam layer is applied an ePTFE tape, which is preferably wrapped helically so that edges overlap somewhat. The ePTFE tape wrapping has the same IND as the substrate (i.e., about 10 microns to about 100 microns), but has a much thinner wall of about 90 microns to about 300 microns. The final thickness of the ePTFE graft is from about 1 mm to about 2 mm, preferably about 1.5 mm.

As the ePTFE tape is wrapped, solvent is simultaneously applied to assist in bonding the tape to the foam (THF or other aprotic solvent is believed to dissolve polyurethane, such that when a small amount is applied during the wrapping process, a mechanical bond is developed therebetween). Tension (e.g., about 100 gram-force to about 200 gram-force) is applied during the wrapping process, which results in the polyurethane working its way into the ePTFE microstructure to assist in the bonding. In this example, the overlapping regions of ePTFE tape do not bond to one another and instead bond to the underlying polyurethane foam, which can allow for longitudinal compliance. However, in another embodiment, the overlapping regions of the tape are adhered to one another. The wrapping of the beading and/or the tape under tension is believed to increase the sealing response of the graft. An optional orientation line can then be applied longitudinally over the length of the graft. The ends of the graft, which to this point have remained uncovered, are now covered with a layer of polyurethane, followed by a helical wrap of beading, which is applied at this stage so that a clinician can remove the beading, if desired, without affecting the embedded beading layer. The beading is applied with solvent to aid in bonding.

Another preferred embodiment, in which the processing methods and equipment described above are utilized unless noted otherwise, is now described. An ePTFE substrate with a carbon lined inner surface is extruded with an orientation line (also made of carbon) and longitudinally expanded such that the final internodal distance (IND) is from about 10 microns to about 40 microns and the wall thickness is from about 100 microns to about 500 microns, preferably about 200 microns. The ePTFE substrate is positioned over a mandrel and the mandrel is rotated as two passes of a polycarbonate polyurethane with solvent are applied to the entire length of the substrate. After the first pass, the substrate is longitudinally compressed about 20% and maintained at this length while the second pass is applied to the entire substrate length, whereby the substrate remains at about 80% of its original length due to the effects of the polyurethane. The two passes of polyurethane form a sealant layer on the graft, having a thickness from about 10 microns to about 150 microns, preferably about 100 microns.

A first polyurethane foam layer is then applied over the polyurethane sealant layer as described above. This first foam layer is applied only to a mid-portion of the substrate, such that each end of the substrate is free of the first foam layer. The distance from the edge of each end of the substrate to the first foam layer is up to about 5 cm. Following the application of the first foam layer, a length of a first beading of polyurethane with barium sulfate is helically wrapped (under tension as described above) over the mid-portion of the substrate containing the first foam layer. The first beading has an elliptical cross-sectional shape with dimensions in the range of about 200 microns to 600 microns high and 200 microns to 1200 microns wide. Evaporation (e.g., by ambient temperature or by heat) is provided to remove the solvent generally before wrapping of the beading. Next, a length of a second beading is helically wrapped (under tension as described above) over each end of the first foam layer, from about 5 cm from the edge of the substrate to about 6 cm from the edge of the substrate. This second beading also has an elliptical cross-sectional shape (which can be circular if the two foci of the ellipse are identical), but has a cross-sectional area smaller than that of the first beading (e.g., a diameter of about 100 microns). After application of the second beading, a second foam layer is applied over the first foam layer and beading along the mid-portion of the substrate, the second foam layer substantially covering the first foam layer without extending longitudinally beyond the first foam layer. The total combined thickness of the first and second foam layers is from about 300 microns to about 1500 microns, preferably about 700 microns.

An ePTFE member, preferably a length of ePTFE tape, is then wrapped about the combined foam layers under tension and passing over or through a dispensing apparatus that applies solvent to the tape prior to the tape contacting the combined foam layers. The edges of the tape preferably overlap somewhat. The ePTFE tape has the same IND as the substrate (i.e., about 10 microns to about 40 microns), but has a much thinner wall of about 100 microns to about 300 microns, preferably about 260 microns. Another length of the second beading is then helically wrapped over each end of the substrate, from about the edge of the substrate to about the edge of the ePTFE tape (which is over the combined foam layers), or over a distance of about 6 cm on each end of the substrate. The two ends of the substrate (i.e., a length of about 6 cm from each edge) are then rapidly dipped in solvent. Two ePTFE generally tubular sleeves each having a length of about 6 cm are prepared and "screwed" over the ends of the substrate (i.e., rotated with force applied so that the sleeves move in a direction toward the mid-portion of the substrate, the second beading acting as "threads") until the second beading is entirely covered and the sleeve extends partially over the edges of the ePTFE tape. The sleeved ends are then rapidly dipped in solvent and the graft is placed in an oven set at about 50° C. air temperature for a time in the range of about 14 hours to about 16 hours.

Figure 16B:
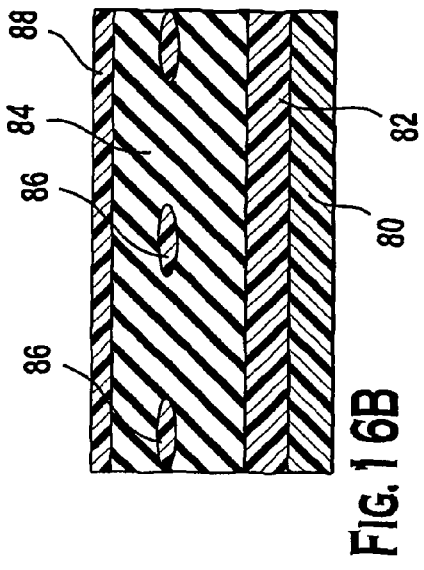
FIG. 16B is a longitudinal cross-sectional view of a mid-portion of a second preferred embodiment of an ePTFE AV graft.
Figure 16D:
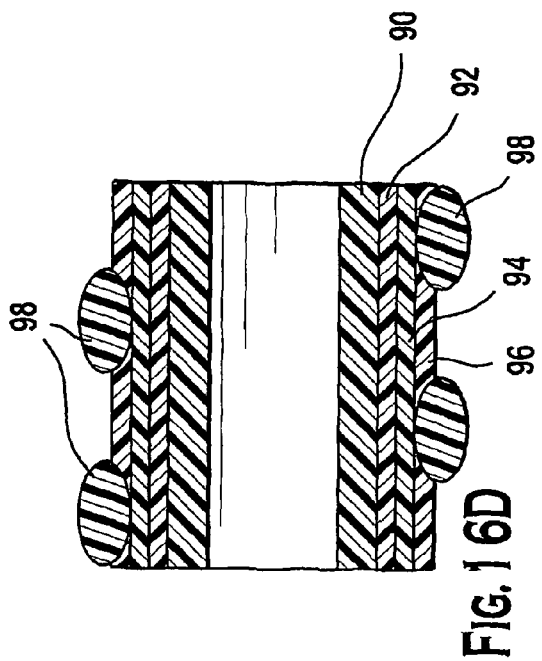
FIG. 16D is a longitudinal cross-sectional view of an end design of the second preferred embodiment of an ePTFE AV graft.
Figure 16A:
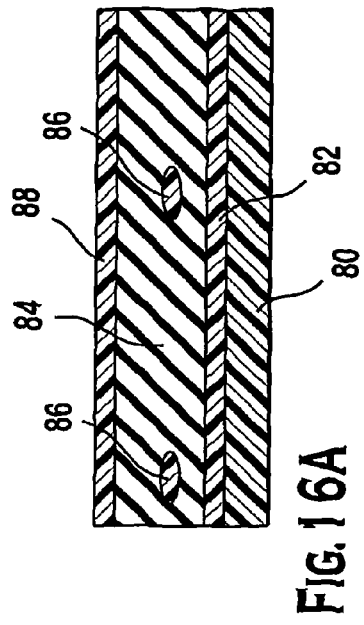
FIG. 16A is a longitudinal cross-sectional view of a mid-portion of a first preferred embodiment of an ePTFE AV graft.
Figure 16C:
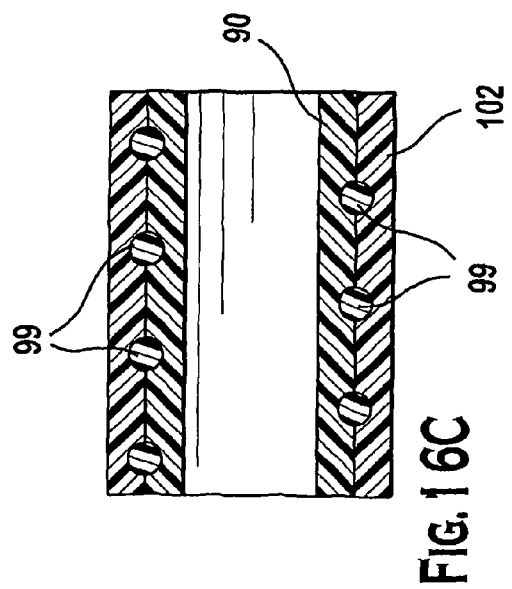
FIG. 16C is a longitudinal cross-sectional view of an end design of the first preferred embodiment of an ePTFE AV graft.

FIGS. 16A-16E illustrate embodiments of ePTFE AV grafts, with FIG. 16A and FIG. 16C representing, respectively, a currently preferred mid-portion and end design. FIGS. 16B and 16D illustrate a previous preferred mid-portion and end design of an ePTFE AV graft. Referring first to FIGS. 16A and 16B, the mid-portion includes an ePTFE substrate 80, over which is disposed a sealant layer 82 (which could include one or more layers as described herein), over which is disposed/formed a foam layer 84 (which, again, could include one or more layers as described herein). Embedded in the foam layer 84 is a beading 86 (i.e., the beading 86 is disposed within a polyurethane matrix) and adhered to the surface of the foam layer 84 and covering the foam layer 84 is an ePTFE member 88. The graft of FIG. 16A is different than the graft of FIG. 16B in at least the following ways: 1) the beading thickness is reduced about 16%; 2) the thickness of the sealant layer 82 is reduced by about 67%, 3) the beading 86 is moved about 44% closer to the sealant layer 82; 4) the thickness of the foam layer is reduced about 26%; and 5) the spacing between turns of the beading is increased about 18%. These changes resulted in a reduced profile graft that improved the functioning of the graft.

With respect to FIGS. 16C and 16D, the end design of the ePTFE AV graft was also changed to improve graft functionality and performance. In the previous end design shown in FIG. 16D, a first sealant layer 92 was dispensed over an ePTFE substrate 90, followed by an ePTFE tape layer 94, and a second sealant layer 96 disposed over the ePTFE tape layer 94. A beading 98 was then wrapped over the second sealant layer 96 and adhered thereto. In the new design shown in FIG. 16C, a beading 99 of smaller cross-sectional area than beading 98 is wrapped directly over the ePTFE substrate 90, adhered thereto by methods and processes described herein. An ePTFE sleeve 102, rather than an ePTFE tape wrap, is then pushed or screwed over the beading 99, resulting in a much lower profile for the end of the graft. The adherence of the ePTFE sleeve 102 to the ePTFE substrate 90 can also be accomplished by spiral wrapping the substrate 90 with beading 99, disposing the sleeve 102 over the beading 99, and spraying a suitable solvent such as THF onto the outer surface of the sleeve 102 so that the solvent penetrates through the outer sleeve 102 and onto the beading 99, which causes the polyurethane portion of the beading 99 to soften and form a bond to both the sleeve 102 and the substrate 90. It is believed that this technique allows for a substantial reduction in the delamination of sleeve 102 from the substrate 90 without having to spray the substrate with solvent or having to soak the beading 99 with solvent.

In the embodiment represented by FIG. 16A, the sealant or base layer 82 is approximately 0.04 mm thick and the foam layer 84 is formed by spraying a first foam layer of about 0.6 mm and drying this first foam layer before spraying a second foam layer so that the total foam layer 84 is about 1.2 mm. In the embodiment represented by FIG. 16C, the beading 90 has an average diameter of about 0.2 mm spaced apart over about 2 mm and disposed proximate the interface between the substrate 90 and the outer sleeve 102 where the outer sleeve 102 is approximately 500 microns.

Figure 16E:
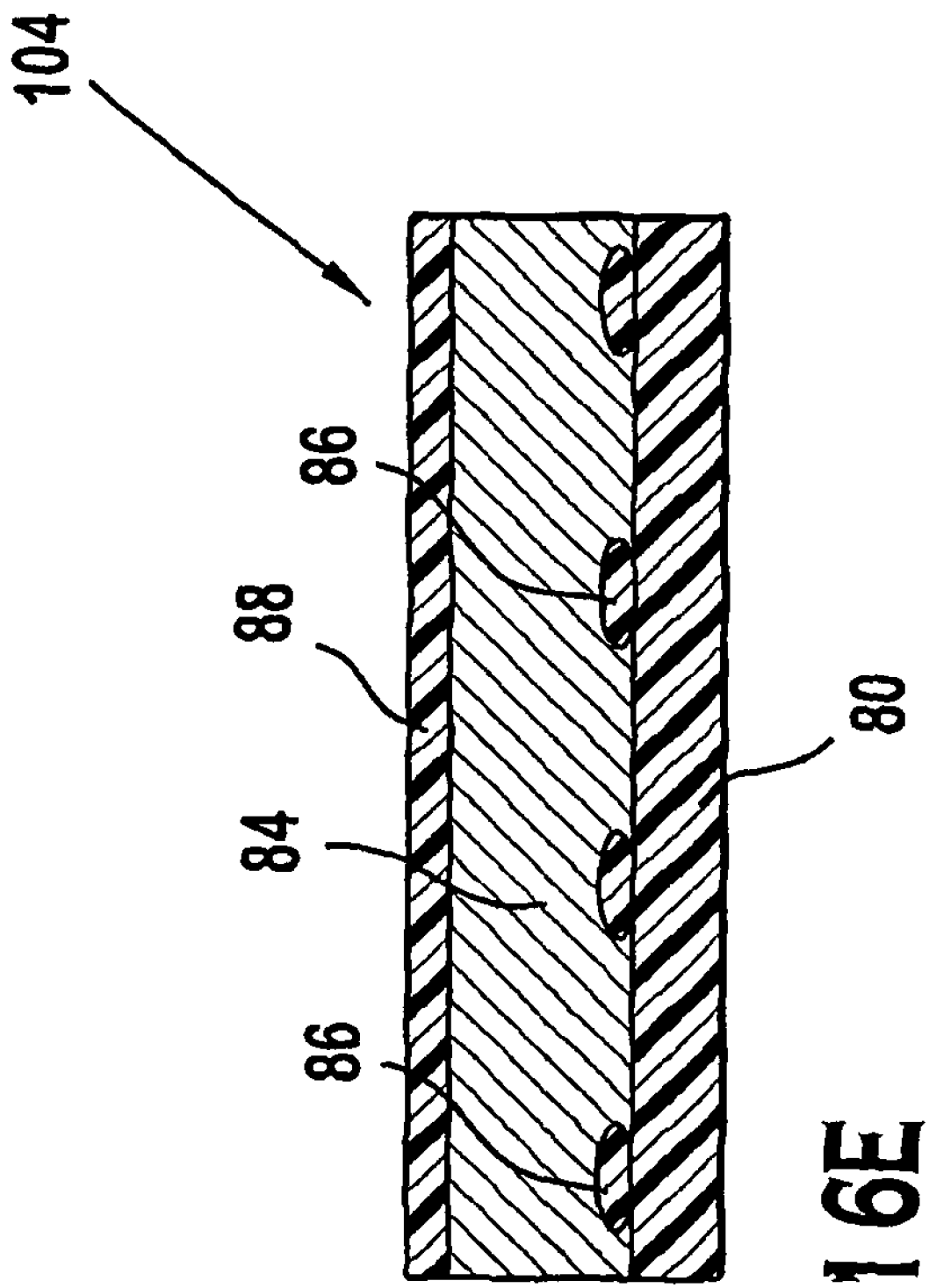
FIG. 16E is a longitudinal cross-sectional view of a mid-portion or central section of another embodiment of an ePTFE AV graft.

FIG. 16E illustrates a currently preferred mid-portion or central section of an ePTFE AV graft. In certain circumstances, a surgeon may desire to clamp a graft by placing a clamping mechanism over the graft to prevent fluid flow through the graft. This clamping action may adversely affect certain properties of an ePTFE AV graft, such as those described in FIGS. 16A-D. In FIG. 16E, a central section 104 of an ePTFE AV graft is constructed differently than that of the remainder of a self-sealing region of the graft. In central section 104, a beading 86 having a relatively large cross-sectional area is positioned directly against the outer surface of, the ePTFE substrate 80 without an intervening sealant layer. In one embodiment, the beading has an elliptical cross-sectional shape with dimensions in the range of about 300 microns to about 700 microns in height and about 200 microns to about 1200 microns in width. In a preferred embodiment the beading 86 is helically wrapped onto the surface of the ePTFE substrate 80 after passing through a bath including a solvent, such as THF, as described in detail above. A foam layer is then disposed onto the ePTFE substrate over the beading, as described above. In one embodiment, a sealing layer is disposed onto the ePTFE substrate over the beading prior to disposition of the foam layer.

Self-Sealing Cuff Graft

The various graft configurations described herein can also have one or more cuffs provided to aid in attachment to a blood vessel. Vascular grafts with cuffs, cuff configurations and methods and apparatuses for making such cuffs and cuff grafts for attachment to blood vessels are described in U.S. Pat. No. 6,273,912 to Scholz et al., U.S. Pat. No. 6,746,480 to Scholz et al., U.S. Application Publication No. US 2004/0210302 to Scholz et al., U.S. Pat. No. 6,190,590 to Randall et al., U.S. Pat. No. 6,203,735 to Edwin et al., U.S. Pat. No. 5,861,026 to Harris et al., U.S. Pat. No. 6,221,101 to Harris et al., U.S. Pat. No. 6,589,278 to Harris et al., and U.S. Application Publication No. US 2004/0064181 to Harris et al., each of which is commonly assigned and incorporated by reference as if fully set forth herein.

Figure 17:
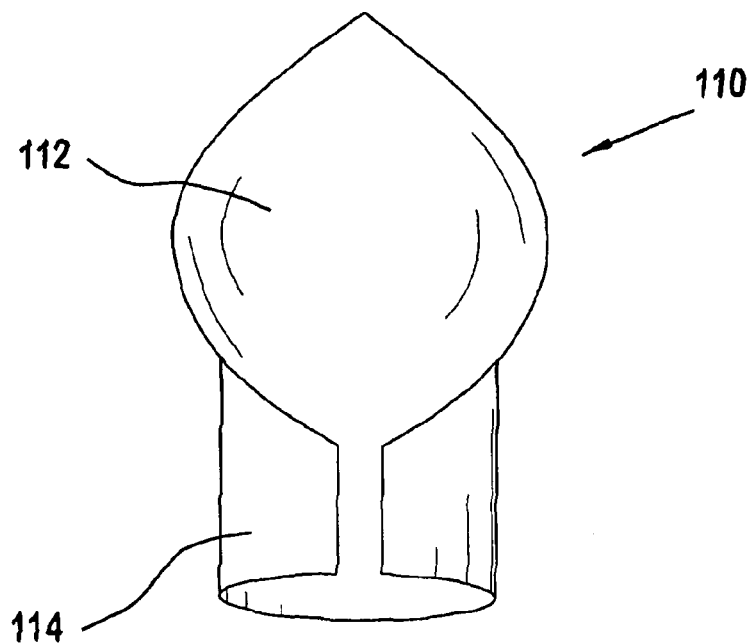
FIG. 17 is a back perspective view of an attachable cuff.

The cuff can be made of ePTFE or other material, such as silicone or polyurethane, and can be bonded to an ePTFE AV graft or a graft having a silicone, polyurethane or other material substrate. One example of a cuff for attachment to a graft is shown in FIG. 17, where a back view of cuff 110 illustrates a cuff section 112 and a neck section 114, wherein the neck section 114 is separated along at least a portion of its length, thus facilitating placement of the cuff over an end of a graft. The cuff 110 can then be bonded to the graft, according to the material properties of each. For instance, in the case that the cuff and graft surface for attachment of the cuff are ePTFE, the cuff can be attached via heating as is known to one of ordinary skill in the art. With respect to embodiments of the ePTFE AV graft described above, the cuff could be placed over one or both ends of the graft at various stages of manufacture. In one embodiment, as with the application of the ePTFE tape wrap, an ePTFE cuff is placed over an end of the graft that has a polyurethane layer applied thereto (e.g., base layer, foam, etc.). A suitable solvent, such as for example, an aprotic solvent including dimethylacetamide (DMSE), dimethylformamide, THF, or their mixtures, is then applied to the neck section of the cuff to dissolve the polyurethane underlying the neck section, which results in bonding of the cuff to the graft. Beading or other processing steps, as discussed herein, would then be possible over the cuff/graft junction.

In another embodiment, a cuff graft is separately formed from an ePTFE AV graft as described herein. The tubular portion of the cuff graft is then attached to the ePTFE AV graft by stretching the wall of the open end of the tubular portion (e.g., via use of an expansion tool) and sliding over one of the ends of the ePTFE AV Graft. In one embodiment, the ePTFE AV graft has external beading, and the open end of the tubular portion of the cuff graft is slid over the ePTFE AV graft until the tubular portion reaches the external beading portion of the ePTFE AV Graft, at which point the tubular portion of the cuff graft is rotated or "screwed" over the external beading. The inner surface of the tubular portion of the cuff graft can have an adhesive thereon to aid in bonding or further bonding can be carried out after the initial attachment step, if desired.

In another embodiment, a self-sealing cuff graft can be created by impregnating polyurethane or a like polymer into the microstructure of an ePTFE cuff graft by vacuum deposition, spray coating, or dip coating procedures as known to a person skilled in the art. Once the polyurethane or like polymer has been introduced, any excess polymer is removed from the exterior of the graft to allow the polyurethane to be formed in the interstices between the nodes and fibrils of the ePTFE. Another embodiment involves spray coating an ePTFE cuff graft with a combination of polymer and solvent as discussed herein, followed by applying an ePTFE tape or patch thereover to create an ePTFE/polymer/ePTFE laminate. In another embodiment, a self-sealing cuff graft is created by connecting a cuff having a neck portion to a graft, dip-coating the graft in a sealant material (e.g., polyurethane) up to the connection point between the graft and neck portion of the cuff, dip-coating both the graft and neck portion in a sealant material (up to the cuff), helically wrapping a beading around the sealant material over the length of the graft and neck portion, and dip-coating the beaded graft and neck portion in a sealant material (up to the cuff).

Figure 18:
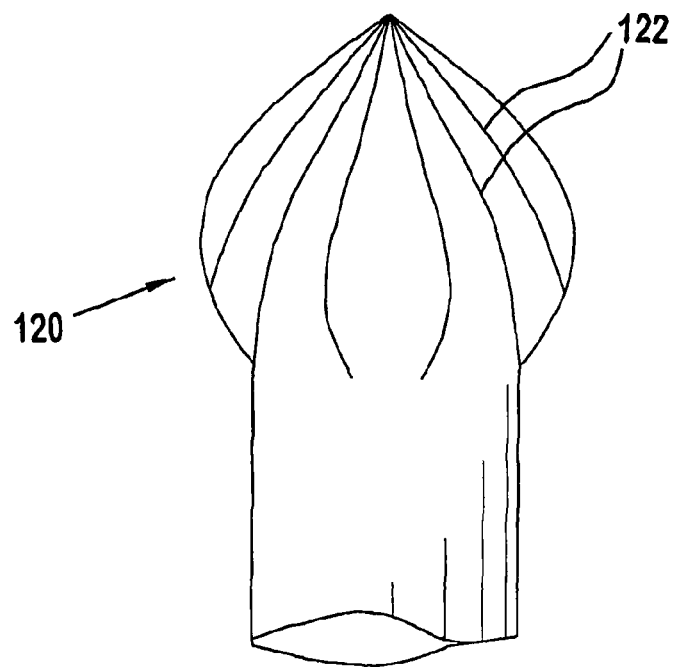
FIG. 18 is a front perspective view of a cuff portion of an ePTFE AV graft with cuff.

In yet another embodiment, the tubular body portion of an ePTFE cuff graft is utilized as the ePTFE substrate for the various processing steps described herein to impart self-sealing, kink-resistance, etc. to the graft. The cuff portion of the ePTFE cuff graft can be on one or both ends of the graft and can have a sealant layer applied thereto or can remain unprocessed. For example, the cuff portion can have a polyurethane coating to maintain the cuff shape. In the event that the cuff portion has a sealant layer applied thereto, the sealant material (e.g., polymer) can be applied in a pattern. In one embodiment, a polymer applied to the cuff portion of an ePTFE AV graft (with cuff) is done so in a pattern of "ridges" on the top of the cuff, as illustrated in FIG. 18. The polymer, such as, for example, polyurethane, at the ridge portions 122 of the cuff 120 provide suture regions for a clinician to mitigate or prevent suture hole bleeding upon attachment to a blood vessel. These ridge portions can be created, for example, by placing a mask over the cuff before the polymer is applied or by laser cutting ridges into the polymer once it has been applied to the cuff. The ridge portions can take on various configurations and be set at a variety of angles, as a person skilled in the art would appreciate. Moreover, in one embodiment the material used to create the ridges has a radiopaque substance incorporated therein so that the edges of the ePTFE cuff can be readily identified during surgery.

Figure 19:
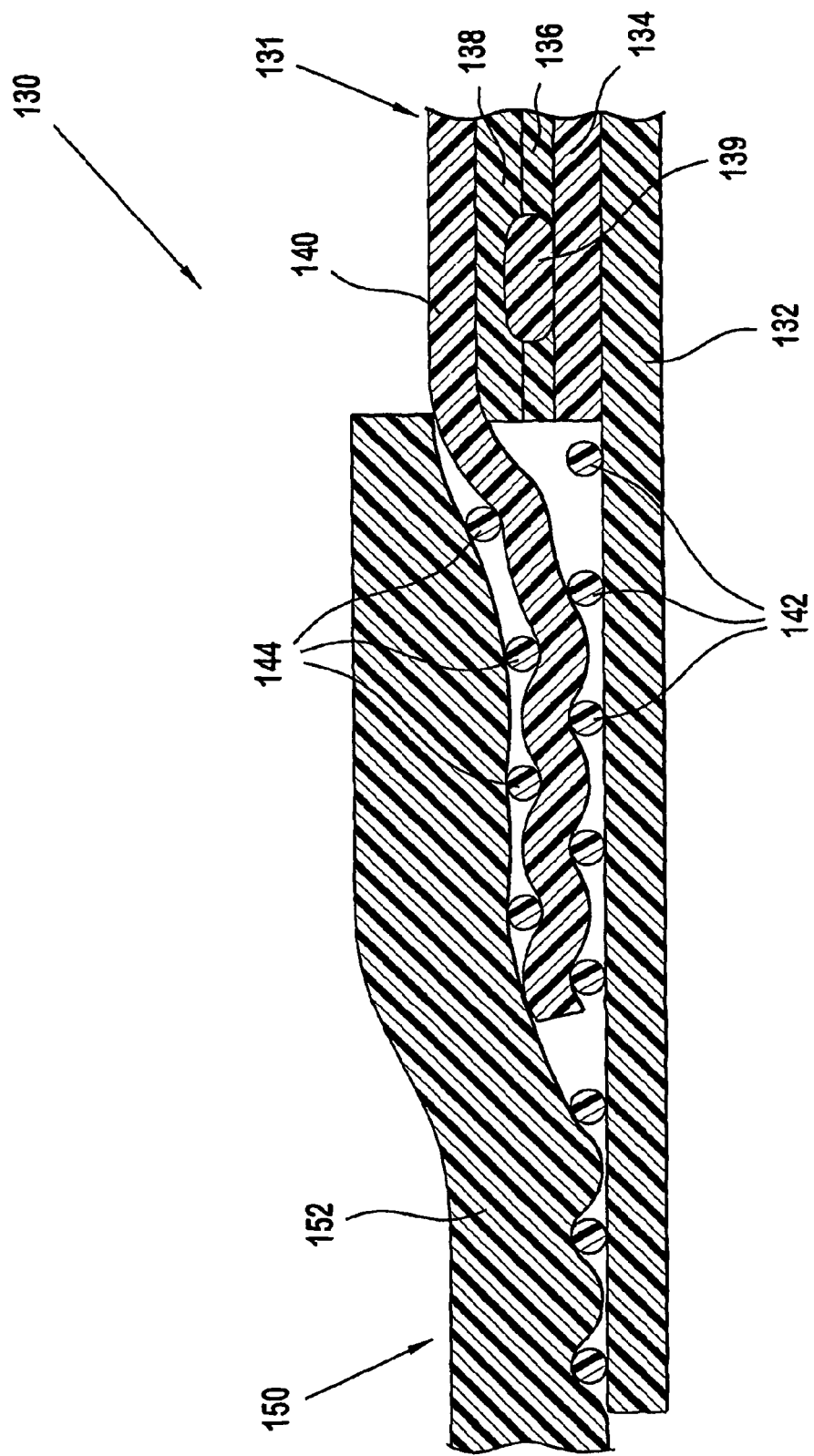
FIG. 19 is a longitudinal cross-sectional view of an end section of one embodiment of an end section of an ePTFE AV cuff graft.

In another embodiment, an ePTFE cuff graft is created by positioning a proximal end of a cuff over an end of an ePTFE AV graft, after a first and second beading have been positioned over the end, as illustrated in FIG. 19. In this embodiment, a double layer of beading is utilized to reinforce the transition between the ePTFE substrate and the cuff. The ePTFE cuff graft 130 includes a self-sealing region 131, including a sealant or base layer 134 disposed onto an ePTFE substrate 132, over which a first foam layer 136 is disposed, followed by a beading 139 and a second foam layer 138. In other embodiments, one or more of the sealant layer 134, first foam layer 136, second foam layer 138 and beading 139 are not included in the self-sealing region 131. Adjacent the self-sealing region 131 at an end of the ePTFE substrate 132 is positioned a beading 142, which contacts the outer surface of the substrate 132. As discussed above, in an embodiment where the beading includes polyurethane, the beading may first be treated or coated with a solvent such as THF to aid in adherence of the beading 142 to the substrate 132. The beading may include, for example, a continuous length of beading that is helically wrapped about the substrate 132 under tension or a plurality of beading rings that are spaced apart along a length of the end of the substrate 132. The distance between adjacent beading rings or windings of the helically wrapped beading in one embodiment is in the range of about 1.2 mm to about 2.8 mm.

An ePTFE member 140 is then positioned over both the self-sealing region 131 and a portion of the beading 142. In one embodiment, as described in detail above, the ePTFE member 140 is a length of ePTFE tape that may first pass through a bath of solvent, such as THF, to aid in bonding the ePTFE tape to one or both of the second foam layer 138 and the beading 142. A beading 144 is then positioned about a length of ePTFE member 140 that covers the beading 142, adjacent the self-sealing region 131. As with the beading 142, the beading 144 may be first treated or coated with a solvent and/or may be helically wrapped about the ePTFE member 140 under tension. In a preferred embodiment, the beading 144 is positioned along the end of the graft such that adjacent rings or windings of the beading 144 are placed between adjacent rings or winding of the beading 142, as illustrated in FIG. 19. In one embodiment, the beading 142 extends over the ePTFE member 140 for a length in the range of about 0.5 cm to about 1.5 cm. Once the beading 144 has been positioned over the ePTFE member 140, a proximal end 152 of a cuff 150 is placed over and bonded to the end of the ePTFE AV graft to form the ePTFE AV cuff graft 130. The cuff 150 may be bonded to the graft using any of the methods discussed above. In a preferred embodiment, the beading 142 and 144 have a circular cross-sectional shape with a cross-sectional area that is substantially equivalent to one another but that is less than the beading 139 in the self-sealing region.

It has been discovered by applicants that the utilization of the elastomeric beading disposed about the ePTFE substrate provides a vascular graft with kink-resistance greater than has been available. Further, it has been discovered that the elimination of a base layer of polyurethane in contact with the ePTFE substrate to effectively increase the thickness of the polyurethane matrix (e.g., polyurethane foam layer) allows the vascular graft to maintain its self-sealing property with essentially the same level of kink-resistance while reducing the adverse effect of any external clamping on the graft. The "kink resistance" or flexibility of a graft can be determined by utilization of the following protocol in relation to FIGS. 20A, 20B and 20C.

Figures 20A, 20B, 20C:
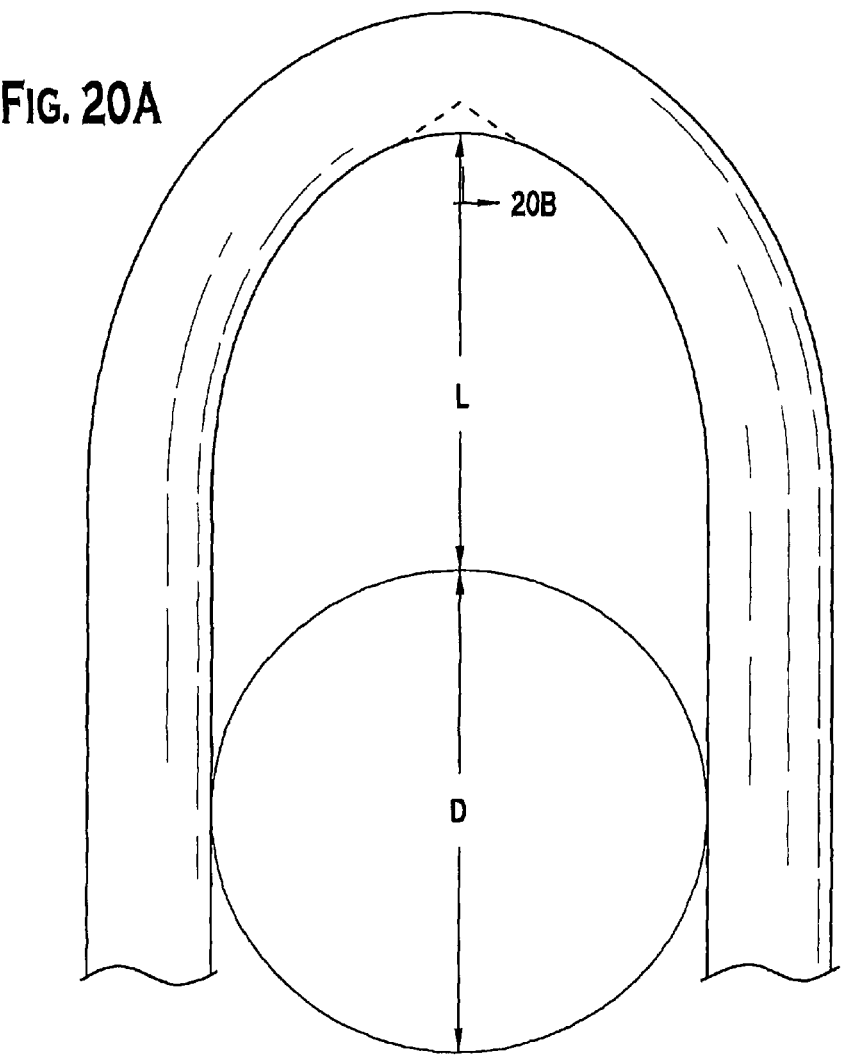
FIG. 20A is a side view of a vascular graft curved about a generally circular pin to illustrate a protocol for determining kink resistance.
FIG. 20B is a cross-sectional view of FIG. 20A along line 20B-20B, illustrating a graft that has not kinked upon bending around the pin.
FIG. 20C is a cross-sectional view of FIG. 20A, showing a change in cross-sectional area of the graft in FIG. 20A due to kinking upon bending around the pin.

In this protocol, a vascular graft is curved about a generally circular pin having a predetermined diameter D. The outer surface of the graft is configured to contact the pin at two tangential locations on the test pin so that the graft defines a curve with an apex of the curve coincident with the outer surface of the graft at a distance L from the closest surface of the pin to the apex where L is approximately the same as D (FIG. 20A). A graft that does not kink thus maintains a cross-sectional area proximate the apex that is essentially the same as a first cross-sectional area of a graft that has not been curved about the pin (FIG. 20B). Kinking is thus defined as the change in cross-sectional area proximate the apex as compared to a graft in a generally linear configuration (i.e., uncurved) (FIG. 20C). It is believed that the more flexible the graft, the more kink resistant the graft becomes. The threshold in which the loss in cross-sectional area due to kinking adversely reduces flow through the graft is defined as a cross-sectional area less than about 50% of the first cross-sectional area, and preferably about 66% of the first cross-sectional area of an uncurved graft for a given diameter of the test pin. It should be noted that the cross-sectional area can be determined in a circular cross-section graft by utilizing the inside diameter of the graft using the formula for circular area (radius squared times the constant pi). However, for ease of calculations, the outside diameter of the graft can be used instead.

Several embodiments of the grafts described herein were tested using the above protocol with a pin diameter D starting with 60 millimeters, 50 millimeters, 20 millimeters and 15 millimeters. The grafts were able to maintain a cross-sectional area of at least about 50% for pins at 60 mm, 50 mm, 20 mm and 15 mm. It is believed that heretofore applicants are the first to provide for an ePTFE vascular graft with elastomeric beading that is resistant to kinking in that the graft is able to maintain a cross-sectional flow area of at least about 50% with test pin diameters of 20 mm and 15 mm in conjunction with the test protocol discussed above. Furthermore, it is believed that applicants are the first to provide for a self-sealing vascular graft having an ePTFE substrate and elastomeric beading resistant to kinking in that the graft is able to maintain a cross-sectional flow area of at least about 50% with test pin diameters of 20 mm and 15 mm.

To further simulate clinical use of the grafts where grafts are usually clamped thus increasing the susceptibility to kinking, such grafts were clamped with a toothed clamp for 45 minutes, massaged by hand towards the circular cross-sectional area for about 5 seconds and tested within about 10 minutes of clamping. The embodiments of the vascular grafts described and shown in relation to FIG. 16E were able to maintain its resistance to kinking by maintaining its cross-sectional flow area of at least 50% of the original cross-sectional area in an uncurved graft for test pin diameters of 20 mm and 15 mm.

Although the preferred embodiments have been described in relation to Carbothane® PC-2585, available from Polymer Technology Group, other suitable polyurethanes, such as, for example, Bionate®, Chronoflex® C (Cardiotech) with a hardness of 93 Shore A, polycarbonate diol (1,6-hexanediol), 14,4-methylene bisphenyl diisocyanate urethane with 1,4-butanediol/dimethylsilane (molecular weight of the soft segment of the polyurethane of about 1000 to about 3000). The weight-average molecular weight (MW) for a suitable polyurethane (i.e., the entire polymer) is in the range of about 25,000 g/mole to about 500,000 g/mole, preferably in the range of about 40,000 g/mole to about 150,000 g/mole. In one preferred embodiment, the weight-average molecular weight is about 50,000 g/mole. Finally, it is noted that the beading on the graft as described herein (e.g., its stiffness properties) is believed to cause a dialysis needle or introducer sheath to deflect away from the beading and into the graft upon contact with the beading.

This invention has been described and specific examples of the invention have been portrayed. While the invention has been described in terms of particular variations and illustrative figures, those of ordinary skill in the art will recognize that the invention is not limited to the variations or figures described. For example, the ePTFE tape or wrap does not have to be utilized with the foam layer in order to achieve the self-sealing functionality of the vascular graft. Moreover, the spraying of polyurethane as described and illustrated herein can be utilized for applications other than applying polyurethane onto a graft substrate, such as, for example, spraying polyurethane onto a stent to produce a covered stent, spraying polyurethane onto both surfaces of a stent to produce an encapsulated stent, spraying a material such as polyurethane onto a frame to create a filter, etc. As one exemplary embodiment, a thrombotic material is incorporated into the foam layer. In another embodiment, the methods, processes and materials described herein to create a graft are applied to a patch for carotid applications in order to reduce suture hole bleeding. In yet another embodiment, the features described and illustrated herein can be applicable to implantable prosthesis other than a self-sealing graft such as, for example, a covered stent, a stent-graft or a partly covered stent.

In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A self-sealing vascular graft, comprising:
a generally tubular ePTFE substrate, including a proximal end section, a distal end section and a central section positioned between the proximal end section and distal end section, the proximal end section and distal end section including a self-sealing region;
a first beading contiguous to a surface of the ePTFE substrate along the central section, the first beading having an elliptical cross-sectional shape with a first cross-sectional area and a solvent disposed on an outer surface thereof; and
a second beading along the proximal section, the second beading having a second cross-sectional area less than the first cross-sectional area.

2. The vascular graft according to claim 1, wherein the central section has a length in the range of about 5 cm to about 12 cm.

3. The vascular graft according to claim 1, wherein the self-sealing region includes a sealant layer having a thickness in the range of about 10 microns to about 300 microns.

4. The vascular graft according to claim 1, wherein the central section includes a foam layer disposed onto the ePTFE substrate over the first beading.

5. The vascular graft according to claim 1, wherein the proximal end section, the distal end section and the central section comprise an outer ePTFE member.

6. The vascular graft according to claim 5, wherein one of the distal and proximal end sections comprises another ePTFE member surrounding at least a portion of the outer ePTFE member.

7. The vascular graft according to claim 1, further comprising a radiopaque material selected from the group consisting essentially of barium sulfate, bismuth subcarbonate, bismuth trioxide, tungsten, or tantalum and combinations thereof.

8. A vascular graft, comprising:
a generally tubular ePTFE substrate defining a longitudinal axis;

a layer of polyurethane matrix disposed about the ePTFE substrate;

a first beading having a first cross-sectional area disposed in the polyurethane matrix along a mid-portion of the ePTFE substrate; and a second beading having a second cross-sectional area less than the first cross-sectional area, the second beading spaced apart from the first beading.

9. The vascular graft according to claim 8, wherein the first beading and the second beading each have elliptical cross-sectional shapes.

10. The vascular graft according to claim 9, wherein the second beading is helically disposed about a proximal end and a distal end of the ePTFE substrate.

11. The vascular graft according to claim 10, wherein the layer of polyurethane matrix comprises a first foam layer, the second beading disposed over the first foam layer, the vascular graft further comprising a second foam layer disposed only over the mid-portion.

12. A self-sealing vascular cuff graft, comprising:

a generally tubular ePTFE substrate;

a self-sealing region extending along a length of the generally tubular substrate between a first and second end thereof, the self-sealing region including at least one of a sealant layer and a foam layer;

an outer ePTFE member positioned over at least a portion of the self-sealing region;

a first beading positioned over the substrate at the first end adjacent to the self-sealing region, the outer ePTFE member extending over at least a portion of the first beading;

a second beading positioned over the outer ePTFE member at the first end adjacent to the self-sealing region; and a flared vascular cuff having a proximal end positioned over at least a portion of the first and second beadings.

13. The self-sealing vascular cuff graft according to claim 12, wherein the first beading contacts an outer surface of the substrate.

14. The self-sealing vascular cuff graft according to claim 12, wherein the first and second beadings are helically wound such that each winding of the second beading is positioned between adjacent windings of the first beading.

15. The self-sealing vascular cuff graft according to claim 12, wherein at least one of the first and second beadings comprises a plurality of rings spaced apart along a length of the first end.

16. The self-sealing vascular cuff graft according to claim 12, wherein the self-sealing region comprises a third beading having a larger cross-sectional area than both the first and second beadings.

17. The self-sealing vascular cuff graft according to claim 12, wherein the self-sealing region comprises a first foam layer and a second foam layer.

18. The self-sealing vascular cuff graft according to claim 17, wherein a third beading contacts both the first and second foam layers.

* * * * *